(12) United States Patent
Tasker et al.

(10) Patent No.: US 8,008,253 B2
(45) Date of Patent: Aug. 30, 2011

(54) TREATMENT FOR ANXIETY

(76) Inventors: Andrew Tasker, Charlottetown (CA);
Tracy Doucette, Stanhope (CA);
Michael Tymianski, Toronto (CA);
Kenneth Mendoza, Oakland, CA (US);
Michael P. Belmares, San Jose, CA (US);
David Garman, San Jose, CA (US);
Peter S. Lu, Palo Alto, CA (US)

( * ) Notice: Subject to any disclaimer, the term of this patent is extended or adjusted under 35 U.S.C. 154(b) by 209 days.

(21) Appl. No.: 12/165,983

(22) Filed: Jul. 1, 2008

(65) Prior Publication Data
US 2009/0036376 A1 Feb. 5, 2009

Related U.S. Application Data

(60) Provisional application No. 60/947,892, filed on Jul. 3, 2007.

(51) Int. Cl.
*A61K 38/04* (2006.01)

(52) U.S. Cl. ...... 514/8.3; 514/17.7; 514/21.4; 514/21.5; 514/18.1

(58) Field of Classification Search ............ None
See application file for complete search history.

(56) References Cited

U.S. PATENT DOCUMENTS

| | | | |
|---|---|---|---|
| 6,723,838 B1 | 4/2004 | Huganir et al. | |
| 2003/0050243 A1* | 3/2003 | Tymianski | 514/12 |
| 2005/0084880 A1 | 4/2005 | Duman et al. | |
| 2005/0214869 A1 | 9/2005 | Lu et al. | |
| 2005/0288231 A1 | 12/2005 | Liesi | |
| 2006/0167075 A1 | 7/2006 | Pearson et al. | |
| 2006/0216331 A1 | 9/2006 | Lines | |
| 2007/0105902 A1 | 5/2007 | Lindsley et al. | |
| 2009/0176713 A1* | 7/2009 | Tymianski et al. | 514/15 |

FOREIGN PATENT DOCUMENTS

WO WO 2009/006548 A2 1/2009

OTHER PUBLICATIONS

Alberts et al. (1994. Molecular Biology of the Cell pp. 129-130).*
Volke 2003 (Behavioural Brain Research 140:141-147).*
Forestiero 2006. Psychopharmacology 184:166-172.*
Volke 2003. Journal of Physiology and Pharmacology 54:653-660.*
Aarts et al., "Treatment of Ischemic Brain Damage by Perturbing NMDA Receptor PSD-95 Protein," *Science*, 298:846-850 (Abstract) (2002).
PCT/US08/69085, International Search Report mailed Jan. 12, 2009.
PCT/US08/69085, Written Opinion of the International Searching Authority mailed Jan. 12, 2009.

* cited by examiner

*Primary Examiner* — Daniel E Kolker
(74) *Attorney, Agent, or Firm* — Alston and Bird LLP

(57) ABSTRACT

The invention provides methods of treating or effecting prophylaxis of a patient having or at risk of developing symptoms of anxiety in which an effective regime of an agent that inhibits specific binding of PSD95 to an NMDA receptor is administered to a patient.

34 Claims, 2 Drawing Sheets

TREATMENT FOR ANXIETY

CROSS-REFERENCE TO RELATED APPLICATION

The present application is a non-provisional of U.S. Ser. No. 60/947,892 filed Jul. 3, 2007, incorporated by reference in its entirety for all purposes.

REFERENCE TO A "SEQUENCE LISTING," A TABLE, OR A COMPUTER PROGRAM LISTING SUBMITTED IN COMPUTER READABLE FORMAT

The Sequence Listing written in file 026372000210US_SeqList.txt is 40,504 bytes, and was created on Jun. 30, 2008, for the application filed herewith, Tasker et al. "TREATMENT FOR ANXIETY." The information contained in this file is hereby incorporated by reference.

BACKGROUND OF THE INVENTION

Anxiety and depression are major psychiatric disorders of significant clinical and socioeconomic significance. Clinical Depression generally presents alongside Anxiety Disorders, and vise-versa. Rarely does a patient present symptoms of only one or the other.

In the general population, these disorders affect daily performance and correlate with impulse control, financial behaviors, substance abuse and organization. Anxiety is an unpleasant state that involves a complex combination of emotions that include fear, apprehension, and worry. It is often accompanied by physical sensations such as heart palpitations, nausea, chest pain, shortness of breath, or tension headache. Anxiety disorder is a blanket term covering several different forms of abnormal, pathological anxiety, fears, phobias and nervous conditions that may come on suddenly (acute anxiety) and/or gradually over a period of several years (chronic), and may impair or prevent the pursuing of normal daily routines. Anxiety disorders are often debilitating chronic conditions, which can be present from an early age or begin suddenly after a triggering event. They are prone to flare up at times of high stress.

Anxiety is often described as having cognitive, somatic, emotional, and behavioral components (Seligman, Walker & Rosenhan, 2001). The cognitive component entails expectation of a diffuse and uncertain danger. Somatically the body prepares the organism to deal with threat (known as an emergency reaction): blood pressure and heart rate are increased, sweating is increased, bloodflow to the major muscle groups is increased, and immune and digestive system functions are inhibited. Externally, somatic signs of anxiety may include pale skin, sweating, trembling, and pupillary dilation. Emotionally, anxiety causes a sense of dread or panic and physically causes nausea, and chills. Behaviorally, both voluntary and involuntary behaviors may arise directed at escaping or avoiding the source of anxiety. These behaviors are frequent and often maladaptive, being most extreme in anxiety disorders. However, anxiety is not always pathological or maladaptive: it is a common emotion along with fear, anger, sadness, and happiness, and it has a very important function in relation to survival.

Neural circuitry involving the amygdala and hippocampus is thought to underlie anxiety (Rosen & Schulkin, Psychol. Rev., 105(2):325-350, 1998). When confronted with unpleasant and potentially harmful stimuli such as foul odors or tastes, PET-scans show increased bloodflow in the amygdala (Zald & Pardo, PNAS, 94(8):4119-4124, 1997; Zald, Hagen & Pardo, J. Neurophysiol., 87(2):1068-1075, 2002). In these studies, the participants also reported moderate anxiety. This might indicate that anxiety is a protective mechanism designed to prevent the organism from engaging in potentially harmful behaviors.

Conventional treatments for anxiety include behavioral therapy, lifestyle changes and/or pharmaceutical therapy (medications). Most drugs used to treat these disorders are known to have negative side effects that may limit their use, or cause habituation and dependence.

Postsynaptic density-95 protein (PSD-95) couples NMDARs to pathways mediating excitotoxicity and ischemic brain damage (Aarts et al., Science 298, 846-850 (2002)). This coupling was disrupted by transducing neurons with peptides that bind to modular domains on either side of the PSD-95/NMDAR interaction complex. This treatment attenuated downstream NMDAR signaling without blocking NMDAR activity, protected cultured cortical neurons from excitotoxic insults and reduced cerebral infarction volume in rats subjected to transient focal cerebral ischemia. This result has led to the proposal to use peptide antagonists of PSD-95/NMDAR for treating stroke and other diseases mediated by excitotoxicity. No significant side effects have been observed in phase I trials of one such antagonist.

BRIEF SUMMARY OF THE CLAIMED INVENTION

The invention provides methods of treating or effecting prophylaxis of a patient having or at risk of developing symptoms of anxiety, comprising administering to the patient an effective regime of an agent that inhibits specific binding of PSD95 to an NMDA receptor. Optionally, the agent is a chimeric peptide comprising an active peptide having an amino acid sequence consisting of 3-25 amino acids from the C-terminus of an NMDA receptor or a PDZ domain 1 and/or 2 from a PSD-95 receptor linked to an internalization peptide. Optionally, the active peptide has an amino acid sequence comprising [E/D/N/Q]-[S/T]-[D/E/Q/N]-[V/L] (SEQ ID NO:1). Optionally, the active peptide comprises an amino acid sequence selected from the group consisting of ESDV (SEQ ID NO:2), ESEV (SEQ ID NO:3), ETDV (SEQ ID NO:4), ETEV (SEQ ID NO:5), DTDV (SEQ ID NO:6), DTEV (SEQ ID NO:7). Optionally, the active peptide has an amino acid sequence comprising KLSSIETDV (SEQ ID NO:8). Optionally, the chimeric peptide has an amino acid comprising YGRKKRRQRRRKLSSIETDV (SEQ ID NO:9). Optionally, the chimeric peptide has an amino acid sequence consisting of YGRKKRRQRRRKLSSIETDV (SEQ ID NO:9). Optionally, the active peptide has an amino acid sequence comprising KLSSIESDV (SEQ ID NO:10). Optionally, the chimeric peptide has an amino acid sequence comprising YGRKKRRQRRRKLSSIESDV (SEQ ID NO:11). Optionally, the amino acid sequence consists of YGRKKRRQRRRKLSSIESDV (SEQ ID NO:11).

Optionally, the patient is free of diseases other than anxiety requiring treating with the antagonist. Optionally, the patient is free of diseases other than anxiety mediated by excitotoxicity. Optionally, the patient is free of stroke. Optionally, the patient is free of diseases mediated by excitotoxicity. Optionally, the agent is administered responsive to the patient having experienced an event promoting anxiety. Optionally, the patient has an episode of acute anxiety. Optionally, the patient is experiencing a panic disorder. Optionally, the patient has a phobic disorder and is being exposed to or is about to be exposed to the phobia. Optionally, the patient has social anxiety disorder and is being exposed to or is about to be exposed to a social situation that would trigger the disorder. Optionally, the patient has an obsessive-compulsive disorder and is showing symptoms of the disorder. Optionally, the patient has physical sensations of anxiety. Optionally, the physical sensations comprise heart palpitations, nausea, chest pain, shortness of breath, and/or tension headache.

Optionally, the patient has post-traumatic stress syndrome. Optionally, the patient has separation anxiety. Optionally, the agent is administered responsive to the patient experiencing anxiety about a future event. Optionally, the effective regime is administered responsive to diagnosis of anxiety in the patient. Optionally, the method further comprises administering a second regime effective for treatment or effecting prophylaxis of anxiety. Optionally, the second regime comprises administering a second agent. Optionally, the second regime comprises administering talk therapy. In some methods, the patient is human. Optionally, the agent is administered by intravenous infusion or subcutaneously. Optionally, the effective regime is administered after diagnosis of a symptom of anxiety in the patient to relieve the symptom, or arrest or inhibit further development of the symptom. Optionally, the agent is administered together with a pharmaceutically acceptable carrier as a pharmaceutical composition.

Some methods further comprise monitoring the patient to assess the effects of treatment on a symptom and/or sign of anxiety. Optionally, the chimeric peptide is administered at a dose of from 0.05 to 500 mg, optionally 0.1 to 100 mg, 0.5 to 50 mg, or 1-20 mg.

The invention further provides a pharmaceutical composition for prophylaxis or treatment of symptoms of anxiety in a patient comprising a pharmaceutically acceptable carrier and an agent as defined above. Optionally, the pharmaceutical composition bears a label indicating suitability for treating or effecting prophylaxis of symptoms of anxiety.

The invention further provides the use of an agent as defined above in the manufacture of a medicament for treatment or effecting prophylaxis of anxiety.

The invention further provides methods of treating or effecting prophylaxis of symptoms of anxiety a patient suffering from or at risk of anxiety comprising administering to the patient an effective regime of a tSXV peptide linked to an internalization peptide.

DEFINITIONS

Figure 1:
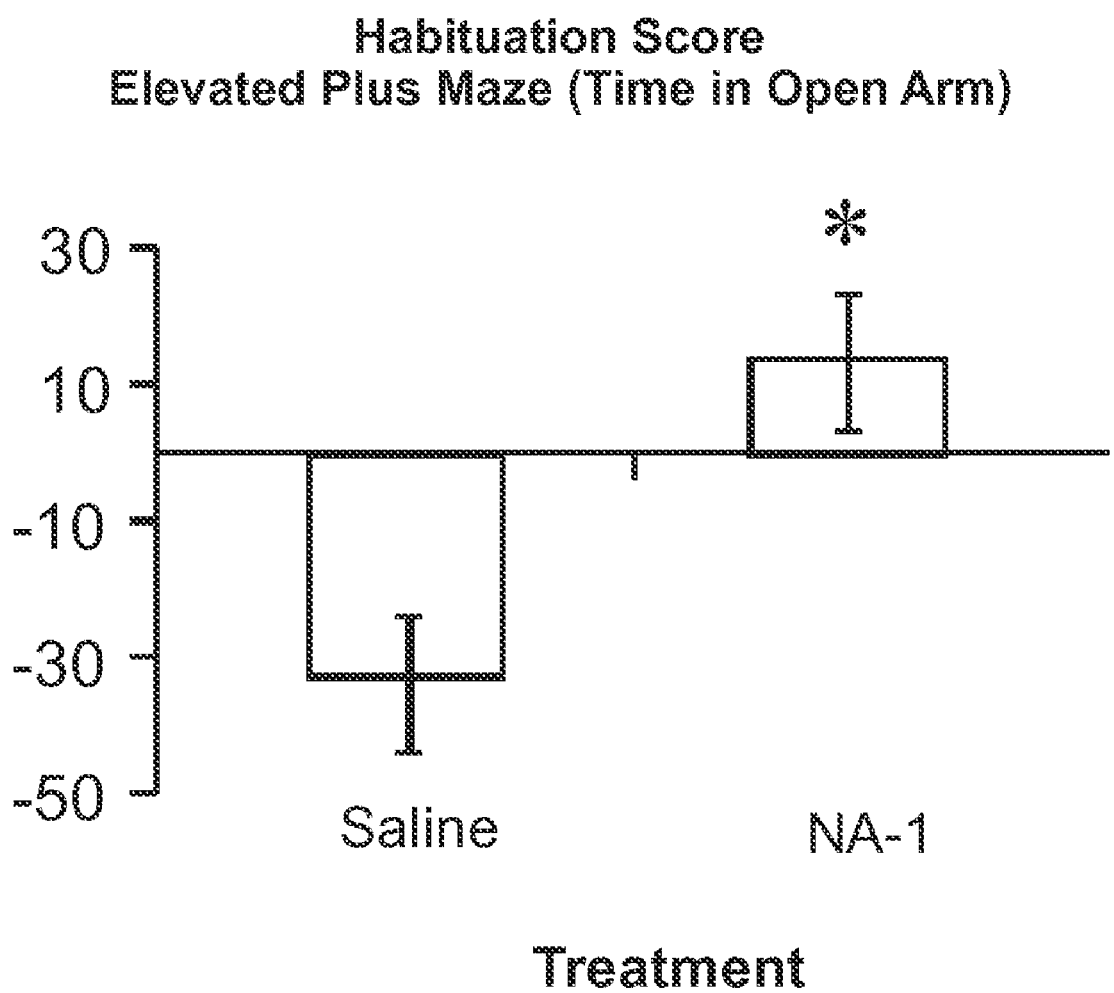
FIG. 1 shows mean habituation score (±SEM) during elevated plus maze testing.

A "chimeric polypeptide" refers to a composite polypeptide, i.e., a single contiguous amino acid sequence, made up of two (or more) distinct, heterologous polypeptides which are not normally fused together in a single amino acid sequence.

The term "PDZ domain" refers to a modular protein domain of about 90 amino acids, characterized by significant sequence identity (e.g., at least 60%) to the brain synaptic protein PSD-95, the Drosophila septate junction protein Discs-Large (DLG), and the epithelial tight junction protein ZO1 (ZO1). PDZ domains are also known as Discs-Large homology repeats ("DHRs") and GLGF repeats. PDZ domains generally appear to maintain a core consensus sequence (Doyle, D. A., 1996, *Cell* 85: 1067-76). Exemplary PDZ domain-containing proteins and PDZ domain sequences disclosed in US 2006-0148711 A1, which is herein incorporated by reference in its entirety.

The term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 3-25 residues, e.g. 3, 4, 5, 8, 10, 12, 14 or 16 residues), forms such a molecular complex. The molecular complex can be observed in vitro using the "A assay" or "G assay" described, e.g., in US 2006-0148711 A1 or in vivo.

A "PL motif" refers to the amino acid sequence of the C-terminus of a PL protein (e.g., the C-terminal 3, 4, 5, 6, 7, 8, 9, 10, 12, 14, 16, 20 or 25 contiguous residues) ("C-terminal PL sequence") or to an internal sequence known to bind a PDZ domain ("internal PL sequence").

A "PL peptide" is a peptide of comprising or consisting of, or otherwise based on, a PL motif that specifically binds to a PDZ domain.

The term "NMDA receptor," or "NMDAR," refers to a membrane associated protein that is known to interact with NMDA. The term thus includes the various subunit forms described in the application. Such receptors can be human or non-human (e.g., mouse, rat, rabbit, monkey).

The terms "isolated" or "purified" means that the object species (e.g., a peptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species.

A "peptidomimetic" and refers to a synthetic chemical compound which has substantially the same structural and/or functional characteristics of a peptide of the invention. The peptidomimetic can contain entirely synthetic, non-natural analogues of amino acids, or, is a chimeric molecule of partly natural peptide amino acids and partly non-natural analogs of amino acids. The peptidomimetic can also incorporate any amount of natural amino acid conservative substitutions as long as such substitutions also do not substantially alter the mimetic's structure and/or inhibitory or binding activity. Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

Statistically significant refers to a p-value that is <0.05, preferably <0.01 and most preferably <0.001.

"Patient" refers to humans, domesticated animals (e.g., cats, dogs), farm animals (e.g., chickens, cows, sheep, horses, pigs), and laboratory animals (e.g., rats, mice).

The term antibody is used to include intact antibodies and binding fragments thereof. Typically, fragments compete with the intact antibody from which they were derived and with other antibodies for specific binding to an antigen.

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity. The term includes an organic or inorganic chemical such a peptide, including antibodies, proteins and small molecules (less than 500 D) and natural products.

The term "symptom" or "clinical symptom" refers to a subjective evidence of a disease, such as a feeling of nausea, as perceived by the patient. A "sign" refers to objective evidence of a disease as observed by a physician, each elevated blood pressure. Symptoms and signs are not necessarily mutually exclusive.

DETAILED DESCRIPTION OF THE INVENTION

I. General

The invention provides agents useful for treating or effecting prophylaxis of symptoms of anxiety. The invention is based in part on results described in the examples in which an antagonist of specific binding of PSD95 to NMDAR 2B was found to reduce anxiety in a rat model of this disorder. Anxiety differs from other diseases in which it has been proposed that such antagonists would be useful in that anxiety is not known to be the result of excitotoxicity. Although an understanding of mechanism is not required for practice of the invention, it is believed that such agents of the invention act at least in part by inhibiting interaction between NMDARs (particularly NAR2A, 2B, 2C and D) with postsynaptic density 95 protein (i.e., PSD-95 inhibitors). The agents may also inhibit interactions between PSD-95 and nNOS (GenBank NM_008712). The agents may also inhibit interactions of PSD95 family members SAP102 (Muller, Neuron 17, 255-265 (1996)), SAP97 (GenBank NM_007862), and PSD93 (GenBank NM_0011807), as well as the PDZ-containing protein TIP1 (GenBank NM_029564). As a result of one or more such inhibitions, it is believed that the agents inhibit excitatory NDMA-mediated neurotransmission in the CNS, and signs and/or symptoms of anxiety resulting from such transmission. Although the methods of the invention can be used for any form of anxiety, they are particularly useful for acute episodes of anxiety, such as panic attacks, which are often the result of a triggering event that has occurred or is expected to occur imminently.

The agents used in the present methods have previously been reported to be useful for treating stroke and have undergone phase I clinical trials for this indication without serious adverse events. The dosages and regimes used for treating stroke can also be used for anxiety, particularly acute episodes of anxiety. More chronic forms of anxiety may require administering of agents for a longer period.

II. Agents

Agents include chimeric peptides and peptidomimetics having at least two components. The first component is an active peptide having an amino acid sequence including or based on the PL motif of a NMDA Receptor (i.e., a PL peptide) or PDZ domain of PSD95. Active peptides useful in the invention inhibit interaction between PDZ domains 1 and 2 of postsynaptic density-95 protein (PSD-95) (human amino acid sequence provided by Stathakism, Genomics 44(1):71-82 (1997)) and the C-terminal PL sequence of one or more NMDA Receptor 2 subunits including the NR2B subunit of the neuronal N-methyl-D-aspartate receptor (Mandich et al., Genomics 22, 216-8 (1994)). NMDAR2B has GenBank ID 4099612, a C-terminal 20 amino acids FNGSSNGH-VYEKLSSIESDV (SEQ ID NO:12) and a PL motif ESDV (SEQ ID NO:2). Active peptides preferably inhibit the human forms of PSD-95 and human NMDAR receptors. However, inhibition can also be shown from species variants of the proteins. A list of NMDA and glutamate receptors that can be used appears below:

TABLE 1

| | | NMDA RECEPTORS WITH PL SEQUENCES | | | |
|---|---|---|---|---|---|
| Name | GI or Acc # | C-terminal 20mer sequence | C-terminal 4mer sequence | internal PL? | PL ID |
| NMDAR1 | 307302 | HPTDITGPLNLSDPSVSTVV (SEQ ID NO: 13) | STVV (SEQ ID NO: 27) | X | AA216 |
| NMDAR1-1 | 292282 | HPTDITGPLNLSDPSVSTVV (SEQ ID NO: 13) | STVV (SEQ ID NO: 27) | X | AA216 |
| NMDAR1-4 | 472845 | HPTDITGPLNLSDPSVSTVV (SEQ ID NO: 13) | STVV (SEQ ID NO: 27) | X | AA216 |
| NMDAR1-3b | 2343286 | HPTDITGPLNLSDPSVSTVV (SEQ ID NO: 13) | STVV (SEQ ID NO: 27) | X | AA216 |
| NMDAR1-4b | 2343288 | HPTDITGPLNLSDPSVSTVV (SEQ ID NO: 13) | STVV (SEQ ID NO: 27) | X | AA216 |
| NMDAR1-2 | 11038634 | RRAIEREEGQLQLCSRHRES (SEQ ID NO: 14) | HRES (SEQ ID NO: 28) | | |

TABLE 1-continued

NMDA RECEPTORS WITH PL SEQUENCES

| Name | GI or Acc # | C-terminal 20mer sequence | C-terminal 4mer sequence | internal PL? | PL ID |
|---|---|---|---|---|---|
| NMDAR1-3 | 11038636 | RRAIEREEGQLQLCSRHRES (SEQ ID NO: 14) | HRES (SEQ ID NO: 28) | | |
| NMDAR2C | 6006004 | TQGFPGPCTWRRISSLESEV (SEQ ID NO: 15) | ESEV (SEQ ID NO: 3) | X | AA180 |
| NMDAR3 | 560546 | FNGSSNGHVYEKLSSIESDV (SEQ ID NO: 12) | ESDV (SEQ ID NO: 2) | X | AA34.1 |
| NMDAR3A | 17530176 | AVSRKTELEEYQRTSRTCES (SEQ ID NO: 16) | TCES (SEQ ID NO:) | | |
| NMDAR2B | 4099612 | FNGSSNGHVYEKLSSIESDV (SEQ ID NO: 12) | ESDV (SEQ ID NO: 29) | X | |
| NMDAR2A | 558748 | LNSCSNRRVYKKMPSIESDV (SEQ ID NO: 17) | ESDV (SEQ ID NO: 2) | X | AA34.2 |
| NMDAR2D | 4504130 | GGDLGTRRGSAHFSSLESEV (SEQ ID NO: 18) | ESEV (SEQ ID NO: 2) | X | |
| Glutamate receptor delta 2 | AF009014 | QPTPTLGLNLGNDPDRGTSI (SEQ ID NO: 19) | GTSI (SEQ ID NO: 30) | X | |
| Glutamate receptor 1 | 128953 | MQSIPCMSHSSGMPLGATGL (SEQ ID NO: 20) | ATGL (SEQ ID NO: 31) | X | |
| Glutamate receptor 2 | L20814 | QNFATYKEGYNVYGIESVKI (SEQ ID NO: 21) | SVKI (SEQ ID NO: 32) | X | |
| Glutamate receptor 3 | AF167332 | QNYATYREGYNVYGTESVKI (SEQ ID NO: 22) | SVKI (SEQ ID NO: 32) | X | |
| Glutamate receptor 4 | U16129 | HTGTAIRQSSGLAVIASDLP (SEQ ID NO: 23) | SDLP (SEQ ID NO: 33) | | |
| Glutamate receptor 5 | U16125 | SFTSILTCHQRRTQRKETVA (SEQ ID NO: 24) | ETVA (SEQ ID NO: 34) | X | |
| Glutamate receptor 6 | U16126 | EVINMHTFNDRRLPGKETMA (SEQ ID NO: 25) | ETMA (SEQ ID NO: 35) | X | |
| Glutamate receptor 7 | U16127 | RRLPGKDSMACSTSLAPVFP (SEQ ID NO: 26) | PVFP (SEQ ID NO: 36) | | |

Some active peptides inhibit interactions between PSD-95 and multiple NMDAR subunits. In such instances, use of the peptide does not necessarily require an understanding of the respective contributions of the different NMDARs to excitatory neurotransmission. Other active peptides are specific for a single NMDAR.

Active peptides include or are based on a PL motif from the C-terminus of any of the above subunits and have an amino acid sequence comprising [S/T]-X-[V/L]. This sequence preferably occurs at the C-terminus of the peptides of the invention. Preferred peptides have an amino acid sequence comprising [E/D/N/Q]-[S/T]-[D/E/Q/N]-[V/L] (SEQ ID NO:1) at their C-terminus. Exemplary peptides comprise: ESDV (SEQ ID NO:2), ESEV (SEQ ID NO:3), ETDV (SEQ ID NO:4), ETEV (SEQ ID NO:5), DTDV (SEQ ID NO:6), and DTEV (SEQ ID NO:7) as the C-terminal amino acids. Two particularly preferred peptides are KLSSIESDV (SEQ ID NO:10), and KLSSIETDV (SEQ ID NO:8). Peptides of the invention without an internalization peptide usually have 3-25 amino acids, peptide lengths (also without an internalization peptide) of 5-10 amino acids, and particularly 9 amino acids are preferred. In some such active peptides, all amino acids are from the C-terminus of an NMDA receptor.

Other active peptides include PDZ domain 1 and/or 2 of PSD-95 or a subfragment of any of these that inhibits interactions between PSD-95 and an NMDA receptor, such as NMDA 2B. Such active peptides comprise at least 50, 60, 70, 80 or 90 amino acids from PDZ domain 1 and/or PDZ domain 2 of PSD-95, which occur within approximately amino acids 65-248 of PSD-95 provided by Stathakism, Genomics 44(1): 71-82 (1997) (human sequence) or NP_031890.1, GI:6681195 (mouse sequence) or corresponding regions of other species variants.

Any of the peptides of the invention can be linked, preferably at its N-terminus, to an internalization peptide that facilitates translocation through the plasma membrane of a cell. Examples of these peptide include tat derived from HIV (Vives et al., 1997, *J. Biol. Chem.* 272:16010; Nagahara et al., 1998, *Nat. Med.* 4:1449), antennapedia from Drosophila (Derossi et al., 1994, *J. Biol. Chem.* 261:10444), VP22 from herpes simplex virus (Elliot and D'Hare, 1997, Cell 88:223-233), complementarity-determining regions (CDR) 2 and 3 of anti-DNA antibodies (Avrameas et al., 1998, *Proc. Natl.*

Acad. Sci. U.S.A., 95:5601-5606), 70 KDa heat shock protein (Fujihara, 1999, EMBO J. 18:411-419) and transportan (Pooga et al., 1998, FASEB J. 12:67-77). For example, the HIV TAT internalization peptide YGRKKRRQRRR (SEQ ID NO:37) can be used. Two preferred peptides including this HIV Tat internalization peptide and an active peptide are YGRKKRRQRRRKLSSIETDV (SEQ ID NO:9, Tat-NR2B9c$_{(TDV)}$), and YGRKKRRQRRRKLSSIESDV (SEQ ID NO:11, Tat-NR2B9c$_{(SDV)}$).

Variants of the standard tat sequence YGRKKRRQRRR (SEQ ID NO:37) can also be used. Co-pending application 60/904,507, filed Mar. 2, 2007 reports that the standard tat peptide binds to and inhibits N-type calcium channels, which binding may lead to a variety of side effects. Although practice of the invention is not dependent on an understanding of mechanism, it is believed that both capacity to cross membranes and binding to N-type calcium channels of tat are conferred by the unusually high occurrence of positively charged residues Y, R and K in the peptide. Variant peptides for use in the invention should retain ability to facilitate uptake into cells but have reduced capacity to bind N-type calcium channels. Some suitable internalization peptides comprise or consist of an amino acid sequence XGRKKRRQRRR (SEQ ID NO:38), in which X is an amino acid other than Y or nothing (in which case G is a free N-terminal residue). A preferred tat variant has the N-terminal Y residue substituted with F. Thus, a tat variant comprising or consisting of FGRKKRRQRRR (SEQ ID NO:39) is preferred. Another preferred variant tat internalization peptide consists of GRKKRRQRRR (SEQ ID NO:40). If additional residues flanking XGRKKRRQRRR (SEQ ID NO:38) are present (beside the active peptide) the residues can be for example, natural amino acids flanking this segment from a tat protein, spacer or linker amino acids of a kind typically used to join two peptide domains, e.g., gly (ser)$_4$ (SEQ ID NO:41), T G E K P (SEQ ID NO:42), GGRRGGGS (SEQ ID NO:43), or LRQRDGERP (SEQ ID NO:44) (see, e.g., Tang et al. (1996), J. Biol. Chem. 271, 15682-15686; Hennecke et al. (1998), Protein Eng. 11, 405-410)), or can be any other amino acids that do not detectably reduce capacity to confer uptake of the variant without the flanking residues and do not significantly increase inhibition of N-type calcium channels relative to the variant without the flanking residues. Preferably, the number of flanking amino acids other than an active peptide does not exceed ten on either side of XGRKKRRQRRR (SEQ ID NO:38). Preferably, no flanking amino acids are present, and the internalization peptide is linked at its C-terminus directly to an active peptide.

Other tat variants that can be used to allow uptake of any of the active peptides of the invention for inhibition of PSD-95 interactions without inhibiting N-type calcium channels include those presented in Table 2 below. It is recommended that these internalization peptides be screened to confirm desired uptake and lack of inhibition of N-type calcium channels. These sequences are predicted herein to maintain transport capability without inhibiting N-type calcium channels and thus allow a greater therapeutic index for the treatment of anxiety.

TABLE 2

| | SEQ ID NOs |
|---|---|
| X-FGRKKRRQRRRKLSSIESDV (F-TatNR2B9c) | 45, 64, 65, 66 |
| X-GKKKKKQKKKKLSSIESDV | 46, 67, 68, 69 |

TABLE 2-continued

| | SEQ ID NOs |
|---|---|
| X-RKKRRQRRRKLSSIESDV | 47, 70, 71, 72 |
| X-GAKKRRQRRRKLSSIESDV | 48, 73, 74, 75 |
| X-AKKRRQRRRKLSSIESDV | 49, 76, 77, 78 |
| X-GRKARRQRRRKLSSIESDV | 50, 79, 80, 81 |
| X-RKARRQRRRKLSSIESDV | 51, 82, 83, 84 |
| X-GRKKARQRRRKLSSIESDV | 52, 85, 86, 87 |
| X-RKKARQRRRKLSSIESDV | 53, 88, 89, 90 |
| X-GRKKRRQARRKLSSIESDV | 54, 91, 92, 93 |
| X-RKKRRQARRKLSSIESDV | 55, 94, 95, 96 |
| X-GRKKRRQRARKLSSIESDV | 56, 97, 98, 99 |
| X-RKKRRQRARKLSSIESDV | 57, 100, 101, 102 |
| X-RRPRRPRRPRRKLSSIESDV | 58, 103, 104, 105 |
| X-RRARRARRARRKLSSIESDV | 59, 106, 107, 108 |
| X-RRRARRRARRKLSSIESDV | 60, 109, 110, 111 |
| X-RRRPRRRPRRKLSSIESDV | 61, 112, 113, 114 |
| X-RRPRRPRRKLSSIESDV | 62, 115, 116, 117 |
| X-RRARRARRKLSSIESDV | 63, 118, 119, 120 |

X can represent a free amino terminus, a biotin molecule or other capping moiety including, but not limited to, H, acetyl, benzoyl, alkyl group (aliphatic), pyroglutamate, alkyl group with cycloalkyl group at the end, biotin with alkyl spacer, (5,6)-FAM. Chemical coupling of the capping group to the N-terminal peptide can be through an amide chemistry, sulphamide chemistry, sulphone chemistry, alkylation chemistry. In addition, X can also be an amino acid other that tyrosine.

Internalization peptides are usually linked to active peptides as fusion peptides, but can also be joined by chemical linkage. Coupling of the two constituents can be accomplished via a coupling or conjugating agent. Numerous such agents are commercially available and are reviewed by S. S. Wong, Chemistry of Protein Conjugation and Cross-Linking, CRC Press (1991). Some examples of cross-linking reagents include J-succinimidyl 3-(2-pyridyldithio) propionate (SPDP) or N,N'-(1,3-phenylene) bismaleimide; N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Peptides of the invention, optionally fused to internalization domains, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; Ostresh (1996) *Methods Enzymol.* 267:220-234.

Peptides of the invention without an internalization peptide usually have 3-25 amino acids, Peptide lengths (also without an internalization peptide) of 5-10 amino acids, and particularly 9 amino acids are preferred.

Appropriate pharmacological activity of peptides or peptidomimetics can be confirmed, if desired, using the animal model described in the Examples. Optionally, peptides or peptidomimetics can also be screened for capacity to inhibit interactions between PSD-95 and NMDAR 2B using assays described in e.g., US 20050059597, which is incorporated by reference. Useful peptides typically have IC50 values of less than 50 uM, 25 μM, 10 uM, 0.1 μM or 0.01 μM in such an assay. Preferred peptides typically have an IC50 value of between 0.001-1 μM, and more preferably 0.05-0.5 or 0.05 to 0.1 μM Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Agents also include small molecules that inhibit interactions between PSD95 and NMDAR 2B, and/or other interactions described above. Suitable small-molecule inhibitors are described in co-pending International Application No. PCT/US2006/062715, which was filed on 29 Dec., 2005, herein incorporated by reference in its entirety. These molecules were identified by in silico screening of a compound library for binding to PSD95, and binding of exemplary compounds was verified experimentally. Suitable compounds include compounds having the general structure of $P_0$-A-B-C-D-E, where D and E are optional, and $P_0$ is:

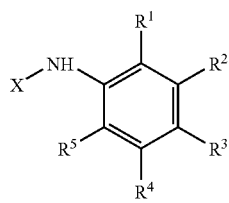

wherein one of $R^1$, $R^2$, $R^3$, $R^4$, and $R^5$ is —COOH, and wherein the remainder of $R^1$, $R^2$, $R^3$, $R^4$, and $R^5$ are selected from the group consisting of F, H, $OCH_3$ and $CH_3$; and X is -A-B-C-D-E, wherein A, B, C, D and E are connected through single bonds and A is selected from the group consisting of C=O, NH, $SO_2$ and $(CH_2)_m$, wherein
m=0, 1, 2, 3, 4, or 5;

B is:

—$OCH_2$—, C=O,

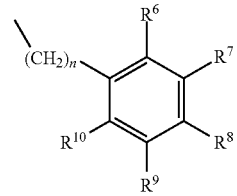

wherein one of $R^6$-$R^{10}$ is bonded to -C-D-E, and wherein the remainder of $R^6$-$R^{10}$ are selected from the group of H, OH, F, Cl, Br, I, $CH_3$, $CH_2CH_3$ and $OCH_3$, and n=0 or 1; or a ring system selected from the group consisting of saturated or unsaturated cycloalkyl or heterocycle; or

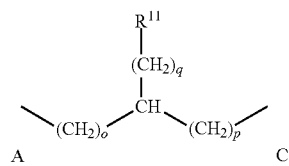

wherein o and p=0 or 1, q=0, 1, 2, 3 or 4, and $R^{11}$ is selected from the group consisting of substituted or unsubstituted lower alkyl, amide, thioether, phenyl, phenol, indole, imidazole, $NH(NH_2)(N(+)H_2)$, COOH, SH, OH, or H;

C is selected from the group consisting of —O—, C=O, NH, CONH, S, phthalamide, $CH_3$, H, $SO_2$ and $(CH_2)_r$, wherein r=0, 1, 2, 3, 4, or 5;

D is optional and when C is not terminating, D is selected from the group consisting of —CN—, C=O, NH, S, O, $SO_2$, $(CH_2)_s$, wherein s=0, 1, 2, 3, 4, or 5, and $(CH_2)_t$—OH, wherein t=0, 1, 2, 3, 4 or 5, and

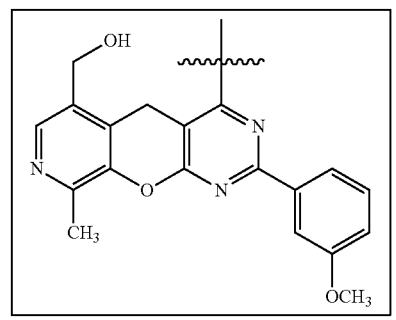

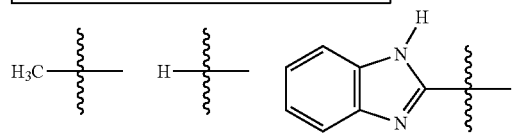

-continued

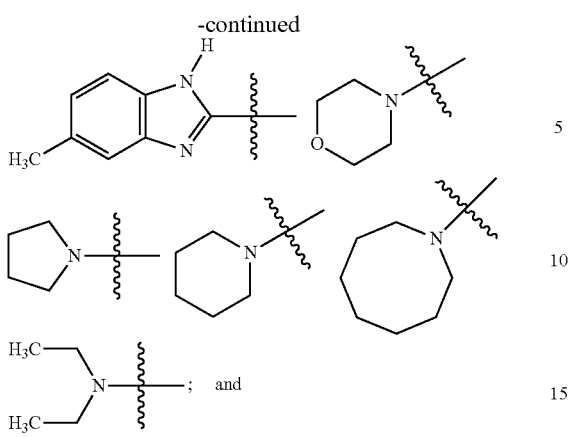

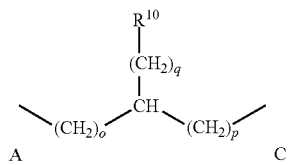

E is optional and when D is not terminating, E is cyclohexyl or phenyl, either substituted with lower alkyl, lower alkoxy, ketone, OH, COOH, nitroso, N-substituted indoline, or a cell membrane translocation peptide; or —(CH$_2$)$_u$—(CHR$^{12}$R$^{13}$), wherein u=0, 1, 2, 3, 4, 5, 6, 7, 8, 9, 10, 11, 12, 13, 14, 15, 16, or 17 and R$^{12}$ and R$^{13}$ are independently selected from the group consisting of H, OH, cyclohexane, cyclopentane, phenyl, substituted phenyl, cyclopentadiene; or branched lower alkyl including isopropyl, isobutyl, 1-isopropyl-2-methyl-butyl, 1-ethyl-propyl; or —NH—COR$^{14}$, wherein R$^{14}$ is (CR$^{15}$R$^{16}$)$_v$H, wherein v=0, 1, 2, 3, 4, 5, 6, 7, 8, 9, 10, 11, 12, 13, 14, 15, 16, or 17 and R$^{15}$ and R$^{16}$ independently selected from the group consisting of H, cyclohexane, phenyl, and a cell membrane translocation peptide.

Alternatively, P$_0$ is:

wherein t=0, 1 or 2, either R$^1$, R$^2$, R$^3$, R$^4$, R$^5$ or R are COOH, and the remainder of R$^1$, R$^2$, R$^3$, R$^4$, R$^5$ and R$^6$ are selected from the group consisting of H, CH$_3$, F, and OCH$_3$, and X is -A-B-C-D-E, wherein A, B, C, D and E are connected through single bonds and A is selected from the group consisting of C=O, SO$_2$, NH, and (CH$_2$)$_m$,
wherein m=0, 1, 2, 3, 4, or 5;

B is:
—OCH$_2$—, C=O; or

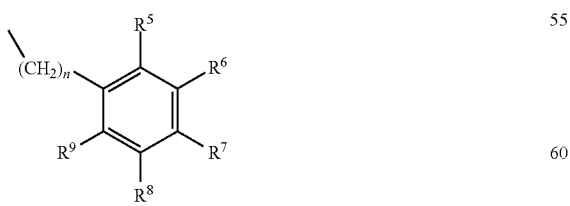

wherein one of R$^5$-R$^9$ is bonded to -C-D-E, and wherein the remainder of R$^5$-R$^9$ are selected from the group of H, OH, F, Cl, Br, I, CH$_3$, CH$_2$CH$_3$ and OCH$_3$, and n=0 or 1; or a ring system selected from the group consisting of saturated or unsaturated cycloalkyl or heterocycle; or

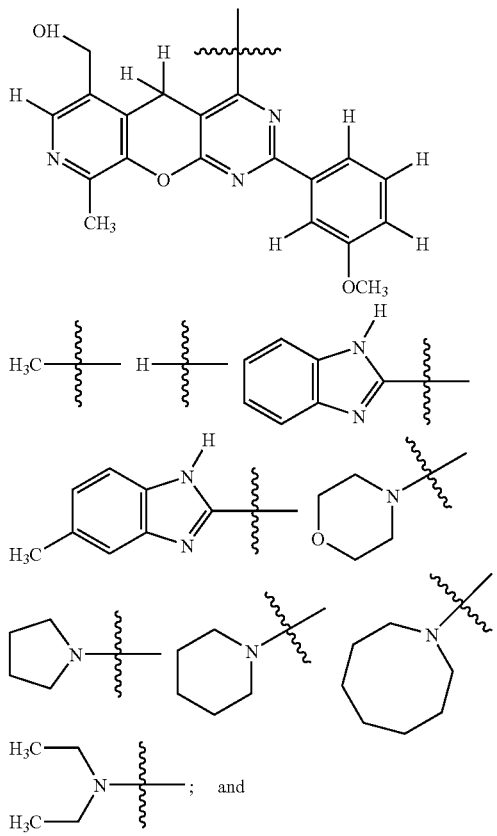

wherein o and p=0 or 1, and R$^{10}$ is selected from the group consisting of substituted or unsubstituted alkyl, amide, thioether, phenyl, phenol, indole, imidazole, NH(NH$_2$)(N(+)H$_2$), COOH, SH, OH, or H;

C is selected from the group consisting of C=O, NH, S, phthalamide, —O—, CH$_3$, H, SO$_2$, and (CH$_2$)$_r$, wherein r=0, 1, 2, 3, 4, or 5;

D is optional and when C is not terminating, D is selected from the group consisting of C=O, —CN—, NH, S, O, SO$_2$, (CH$_2$)$_s$, wherein s=0, 1, 2, 3, 4, or 5, and E is phenyl or cyclohexyl, either substituted with lower alkyl, lower alkoxy, ketone, OH, COOH, nitroso, N-substituted indoline; or —(CHR$^{11}$R$^{12}$)$_u$, wherein u=0, 1, 2, 3, 4, 5, 6, 7, 8, 9, 10, 11, 12, 13, 14, 15, 16, or 17 and R$^{11}$ and R$^{12}$ are independently selected from the group consisting of H, OH, cyclohexane, cyclopentane, phenyl, substituted phenyl, cyclopentadiene; or branched lower alkyl including isopropyl, isobutyl, 1-isopropyl-2-methyl-butyl, 1-ethyl-propyl; or —NH—COR$^{11}$, wherein R$^{11}$ is (CHR$^{12}$R$^{13}$)$_s$, wherein s=0, 1, 2, 3, 4, 5, 6, 7, 8, 9, 10, 11, 12, 13, 14, 15, 16, or 17 and R$^{12}$ and R$^{13}$ independently selected from the group consisting of H, cyclohexane, phenyl, and a cell membrane translocation peptide.

Some preferred compounds have the following structure:

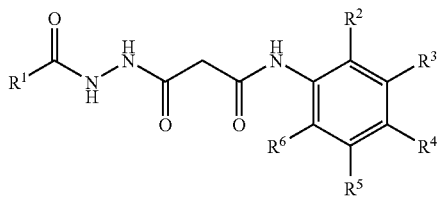

wherein R$^1$ is a member selected from the group consisting of cyclohexyl substituted with 0-4 R$^7$, phenyl substituted with 0-4 R$^7$, —(CH$_2$)$_u$—(CHR$^8$R$^9$), a branched C$_{1-6}$ alkyl (isopropyl, isobutyl, 1-isopropyl-2-methyl-butyl, 1-ethyl-propyl), and —NH—C(O)—(CR$^{10}$R$^{11}$)$_v$H;

each R$^7$ is independently a member selected from the group consisting of C$_{1-6}$ alkyl, C$_{1-6}$ alkoxy, —C(O)R$^{12}$, OH, COOH, —NO, N-substituted indoline and a cell membrane translocation peptide each R$^8$ and R$^9$ is independently selected from the group consisting of H, OH, cyclohexane, cyclopentane, phenyl, substituted phenyl (for instance, substituted with halo, alkyl and/or hydroxyl groups) and cyclopentadiene;

each R$^{10}$ and R$^{11}$ is independently selected from the group consisting of H, cyclohexane, phenyl and a cell membrane translocation peptide;

R$^{12}$ is a member selected from the group consisting of C$_{1-6}$ alkyl and aryl; and each of u and v are independently from 0 to 20;

wherein one of R$^2$, R$^3$, R$^4$, R$^5$ and R$^6$ is —COOH, and wherein the remainder of R$^2$, R$^3$, R$^4$, R$^5$ and R$^6$ are each independently selected from the group consisting of F, H, OCH$_3$ and CH$_3$.

In one embodiment R$^1$ is —(CH$_2$)$_u$—(CHR$^8$R$^9$). In another embodiment, R$^1$ is a member of the above-defined group of R$^1$ substituents other than —(CH$_2$)$_u$—(CHR$^8$R$^9$).

A preferred agent has the following structure

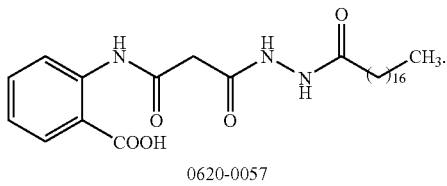

0620-0057

Other compounds can be screened from naturally occurring or synthetic molecules. Agents to be screened can also obtained from natural sources, such as, e.g., marine microorganisms, algae, plants, fungi, Random libraries of peptides or other compounds can also be screened for binding to PSD95 and capacity to inhibit interactions of PSD95 with the NMDARs and/or the molecules described in section I above. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980. Avimers constituting multimers of A-domains can be used in similar fashion to antibodies (Silverman et al. Nat. Biotechnol. 23, 1493-4 (2005)). Compounds with the binding and inhibitory properties described above can be further screened in an animal model of anxiety.

Optionally, any of the above compounds is mixed with a pharmaceutical excipient as a pharmaceutical composition.

III. Anxiety

Unless otherwise apparent from the context, reference to anxiety includes any of the forms of anxiety defined in the Diagnostic and Statistical Manual of Mental Disorders, 4th edition (DSM-IV-TR) and/or below. Many of the subtypes of anxiety are characterized by acute episodes (i.e., relatively short periods of relatively numerous and/or intense symptoms and signs of disease separated by relatively long intervals of fewer or less intense symptoms and signs, if any). Often acute episodes are often triggered by a specific event that has occurred or is expected to occur imminently. Anxiety and its subtypes are usually diagnosed by applying a questionnaire to determine whether patients meet DSM-IV-TR criteria.

Generalized Anxiety Disorder

Generalized anxiety disorder is a common chronic disorder that affects twice as many women as men and can lead to considerable impairment (Brawman-Mintzer & Lydiard, J. Clin. Psychiatry, 57 (Suppl. 7):3-8, 1996; Bull. Menninger Clin., 61(2 suppl. A):A66-A94, 1997; J. Clin. Psychiatry, 58(suppl. 3):16-25, 1997). As the name implies, generalized anxiety disorder is characterized by long-lasting anxiety that is not focused on any particular object or situation. In other words it is unspecific or free-floating. People with this disorder feel afraid of something but are unable to articulate the specific fear. They fret constantly and have a hard time controlling their worries. Because of persistent muscle tension and autonomic fear reactions, they may develop headaches, heart palpitations, dizziness, and insomnia. These physical complaints, combined with the intense, long-term anxiety, make it difficult to cope with normal daily activities.

Panic Disorder

In panic disorder, a person suffers brief attacks of intense terror and apprehension that cause trembling and shaking, confusion, dizziness, nausea, difficulty breathing, and feelings of impending doom or a situation that would be embarrassing. The American Psychiatric Association (2000) defines a panic attack as fear or discomfort that arises abruptly and peaks in 10 minutes or less, and can occasionally last hours.

Although panic attacks sometimes seem to occur out of nowhere, they generally happen after frightening experiences, prolonged stress, or even exercise. Many people who have panic attacks (especially their first one) think they are having a heart attack and often end up at the doctor or emergency room. Even if the tests all come back normal the person will still worry, with the physical manifestations of anxiety only reinforcing their fear that something is wrong with their body. Heightened awareness (hypervigilance) of any change in the normal function of the human body, will be noticed and interpreted as a possible life threatening illness by an individual suffering from panic attacks.

Normal changes in heartbeat, such as when climbing a flight of stairs will be noticed by a panic sufferer and lead them to think something is wrong with their heart or they are about to have another panic attack. Some begin to worry excessively and even quit jobs or refuse to leave home to avoid future attacks. Panic disorder can be diagnosed when several apparently spontaneous attacks lead to a persistent concern about future attacks.

Agoraphobia

A common complication of panic disorder is agoraphobia—anxiety about being in a place or situation where escape is difficult or embarrassing (Craske, 2000; Gorman, 2000). The definition of the word has expanded to refer to avoidance behaviors that sufferers often develop. If a sufferer of panic attacks seems to have them while driving, for example, then he or she may avoid driving, which relieves the anxiety, and subsequently makes future driving more difficult, as a result of behavioral reinforcement.

Phobias

This category involves a strong, irrational fear and avoidance of an object or situation. The person knows the fear is irrational, yet the anxiety remains. Phobic disorders differ from generalized anxiety disorders and panic disorders because there is a specific stimulus or situation that elicits a strong fear response. A person suffering from a phobia of spiders might feel so frightened by a spider that he or she would try to jump out of a speeding car to get away from one.

People with phobias have especially powerful imaginations, so they vividly anticipate terrifying consequences from encountering such feared objects as knives, bridges, blood, enclosed places, certain animals or situations. These individuals generally recognize that their fears are excessive and unreasonable but are generally unable to control their anxiety.

Social Anxiety Disorder

Social anxiety disorder is also known as social phobia. Individuals with this disorder experience intense fear of being negatively evaluated by others or of being publicly embarrassed because of impulsive acts. Almost everyone experiences "stage fright" when speaking or performing in front of a group. Since occasionally there are artists or performers with social anxiety disorder who are able to perform publicly without significant anxiety, their love of performing and practicing their art may be diminishing their anxiety. But people with social phobias often become so anxious that performance, if they are not natural performers, such as children playing musical instruments from a young age, is out of the question. In fact, their fear of public scrutiny and potential humiliation becomes so pervasive that normal life can become impossible (den Boer 2000; Margolis & Swartz, 2001). Another social phobia is love-shyness, which most adversely affects certain men. Those afflicted find themselves unable to initiate intimate adult relationships (Gilmartin 1987).

Obsessive-Compulsive Disorder

Obsessive compulsive disorder is a type of anxiety disorder primarily characterized by obsessions and/or compulsions. Obsessions are distressing, repetitive, intrusive thoughts or images that the individual often realizes are senseless. Compulsions are repetitive behaviors that the person feels forced or compelled into doing, in order to relieve anxiety. The OCD thought pattern may be likened to superstitions: if X is done, Y won't happen—in spite of how unlikely it may be that doing X will actually prevent Y, if Y is even a real threat to begin with. A common example of this behavior would be obsessing that one's door is unlocked, which may lead to compulsive constant checking and rechecking of doors. Often the process seems much less logical. For example, the compulsion of walking in a certain pattern may be employed to alleviate the obsession that something bad is about to happen. Lights and other household items are also common objects of obsession.

Post-Traumatic Stress Disorder

Post-traumatic stress disorder is an anxiety disorder which results from a traumatic experience, such as being involved in battle, rape, being taken hostage, or being involved in a serious accident. The sufferer may experience flashbacks, avoidant behavior, and other symptoms. Post-traumatic stress disorder (PTSD) is a term for certain severe psychological consequences of exposure to, or confrontation with, stressful events that the person experiences as highly traumatic. Clinically, such events involve actual or threatened death, serious physical injury, or a threat to physical and/or psychological integrity, to a degree that usual psychological defenses are incapable of coping with the impact. It is occasionally called post-traumatic stress reaction to emphasize that it is a result of traumatic experience rather than a manifestation of a pre-existing psychological condition. The presence of a PTSD response is influenced by the intensity of the experience, its duration, and the individual person involved.

PTSD may be triggered by an external factor or factors. Its symptoms can include the following: nightmares, flashbacks, emotional detachment or numbing of feelings (emotional self-mortification or dissociation), insomnia, avoidance of reminders and extreme distress when exposed to the reminders ("triggers"), loss of appetite, irritability, hypervigilance, memory loss (may appear as difficulty paying attention), excessive startle response, clinical depression, and anxiety. It is also possible for a person suffering from PTSD to exhibit one or more other comorbid psychiatric disorders; these disorders often include clinical depression (or bipolar disorder), general anxiety disorder, and a variety of addictions.

Symptoms that appear within the first month of the trauma are called Acute stress disorder, not PTSD according to DSM-IV. If there is no improvement of symptoms after this period of time, PTSD is diagnosed. PTSD has three subforms: Acute PTSD subsides after a duration of three months. If the symptoms persist, the diagnosis is changed to chronic PTSD. The third subform is referred to as delayed onset PTSD which may occur months, years, or even decades after the event.

PTSD first appeared in the Diagnostic and Statistical Manual of Mental Disorders (DSM) in 1980. War veterans are the most publicly-recognized victims of PTSD; long-term psychiatric illness was formally observed in World War I veterans. PTSD has also been recognized as a problem for marginalized groups within societies. One such group is Australian Aboriginal peoples, and other Indigenous peoples around the world. In these cases the repeated history of childhood and adult trauma, removal of children from their families, interpersonal violence and substance abuse, and early death, results in generations of people with high levels of PTSD.

PTSD is normally associated with trauma such as violent crimes, rape, and war experience. However, there have been a growing number of reports of PTSD among cancer survivors and their relatives (Smith 1999, Kangas 2002). Most studies deal with survivors of breast cancer (Green 1998, Cordova 2000, Amir & Ramati, J. Anxiety Disord., 16(2):195-206, 2002), and cancer in children and their parents (Landolt 1998, Stuber 1998), and show prevalence figures of between five and 20%. Characteristic intrusive and avoidance symptoms have been described in cancer patients with traumatic memories of injury, treatment, and death (Brewin 1998). There is yet disagreement on whether the traumas associated with different stressful events relating to cancer diagnosis and treatment actually qualify as PTSD stressors (Green 1998). Cancer as trauma is multifaceted, includes multiple events that can cause distress, and like combat, is often characterized by extended duration with a potential for recurrence and a varying immediacy of life-threat (Smith 1999).

Separation Anxiety

Separation Anxiety affects school aged children who struggle to engage socially or participate in the absence of their primary care giver. Separation anxiety can resemble school phobia.

Exposure Anxiety

Exposure Anxiety was first described in the book, Exposure Anxiety; The Invisible Cage by autistic author Donna Williams and referred to the anxiety associated with feeling one's own existence too extremely to withstand. Exposure Anxiety was described as triggering a pervasive self protective state of involuntary avoidance, diversion and retaliation responses resulting in a struggle to do things 'as oneself', 'by oneself' or 'for oneself'. By learning to do things as a 'nonself' those with it could sometimes still do things by taking on other characters, roles and voices. Exposure Anxiety was further distinguished from Avoidant Personality Disorder, Oppositional Defiance Disorder and Demand Avoidance Syndrome in the book The Jumbled Jigsaw.

IV. Patients Amenable to Treatment

Patients amenable to treatment include humans having anxiety as described above and/or as defined by the criteria of the Diagnostic and Statistical Manual (2000) (DSM IV TR) (ISBN 0-89042-024-6) (incorporated by reference). Some such patients experience low level symptoms chronically and others experience acute episodes of intense symptoms separated by periods in which symptoms are absent or much reduced. Treatment can be administered therapeutically while symptoms are present or prophylactically in advance of anticipated development of symptoms in patients considered at heightened risk of developing symptoms, such as for example patients about to undergo an event that has triggered an episode of anxiety previously. Patients also include laboratory animal models of anxiety, such as described in the examples, and domestic and farm animals experiencing anxiety similar to the human condition.

Although the methods of the invention can be practiced on any of the forms of anxiety discussed above, they are most suitable for forms having acute episodes, such as panic disorders, phobias, social anxiety disorder, obsessive compulsive disorders, separation anxiety and posttraumatic disorder and other acute disorders having physical sensations as well as a subjective discomfort. In such disorders, a patient can be treated soon after onset of an acute episode. In some disorders the patient can alternatively or additionally be treated before onset of an acute episode that is expected to result from a triggering event. For example, if a patient with a phobia of a future event (e.g., flying) can be treated before the future event becomes sufficiently imminent that an anxiety episode is triggered.

Some patients have co-morbid depression with anxiety. Patients amenable to treatment may or may not have other diseases or disorders for which treatment with PSD95-NMDAR antagonists has previously been proposed. These diseases and conditions include excitotoxicity mediated diseases, stroke, epilepsy, hypoxia, traumatic injury to the CNS not associated with stroke such as traumatic brain injury and spinal cord injury, Alzheimer's disease and Parkinson's disease. In patients, in which such a comormid disease is present, the agents of the invention can be effective against anxiety and the co-morbid disease.

VI. Methods of Treatment

The agents of the invention are used to treat patients suffering from or at risk of developing symptoms of anxiety as described above. In forms of anxiety having acute episodes, treatment is usually initiated either before a triggering event that promotes the episode or as soon as possible after initiation of the episode. If treatment is administered after an episode has started, the treatment is usually administered within one to six hours after initiation of an episode of anxiety. Often a single dose of an agent of the invention is sufficient. However, multiple doses can also be administered at intervals of 6-24 hr.

The response of the patient to the treatment can be monitored by determining signs and symptoms of anxiety and its subtypes according to the criteria of the DSM-IV-TR.

The methods of the invention can be combined with conventional treatments for anxiety. Such conventional treatments include behavioral therapy, lifestyle changes and/or pharmaceutical therapy. Mainstream treatment for anxiety consists of the prescription of anxiolytic agents and/or antidepressants and/or referral to a cognitive-behavioral therapist (e.g., talk therapy). Conventional drugs include benzodiazepines (such as xanax) and antidepressants of most of the main classes (SSRI, TCAs, MAOIs), and Quetiapine.

VII. Pharmaceutical Compositions, Dosages and Routes of Administration

The peptides and peptidomimetics of the invention can be administered in the form of a pharmaceutical composition. Pharmaceutical compositions are manufactured under GMP conditions. Pharmaceutical compositions can be provided in unit dosage form (i.e., the dosage for a single administration) containing any of the dosages indicated below. Pharmaceutical compositions can be manufactured by means of conventional mixing, dissolving, granulating, dragee-making, levigating, emulsifying, encapsulating, entrapping or lyophilizing processes. In particularly, lypholyized peptides or peptidomimetics of the invention can be used in the formulations and compositions described below.

Pharmaceutical compositions can be formulated in conventional manner using one or more physiologically acceptable carriers, diluents, excipients or auxiliaries that facilitate processing of peptides or peptidomimetics into preparations which can be used pharmaceutically. Proper formulation is dependent on the route of administration chosen.

Administration can be parenteral, intravenous, oral, subcutaneous, intraarterial, intracranial, intrathecal, intraperitoneal, topical, intranasal or intramuscular. Intravenous administration is preferred.

Pharmaceutical compositions for parenteral administration are preferably sterile and substantially isotonic. For injection, peptides or peptidomimetics can be formulated in aqueous solutions, preferably in physiologically compatible buffers such as Hanks's solution, Ringer's solution, or physiological saline or acetate buffer (to reduce discomfort at the site of injection). The solution can contain formulatory agents such as suspending, stabilizing and/or dispersing agents.

Alternatively the peptides or peptidomimetics can be in powder form for constitution with a suitable vehicle, e.g., sterile pyrogen-free water, before use.

For transmucosal administration, penetrants appropriate to the barrier to be permeated are used in the formulation. This route of administration can be used to deliver the compounds to the nasal cavity or for sublingual administration.

For oral administration, the compounds can be formulated by combining the peptides or peptidomimetics with pharmaceutically acceptable carriers as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as the cross-linked polyvinylpyrrolidone, agar, or alginic acid or a salt thereof such as sodium alginate. If desired, solid dosage forms can be sugar-coated or enteric-coated using standard techniques. For oral liquid preparations such as, for example, suspensions, elixirs and solutions, suitable carriers, excipients or diluents include water, glycols, oils, alcohols. Additionally, flavoring agents, preservatives, coloring agents and the like can be added.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions can be used to deliver peptides and petidomimetics. Certain organic solvents such as dimethylsulfoxide also can be employed, although usually at the cost of greater toxicity. Additionally, the compounds can be delivered using a sustained-release system, such as semipermeable matrices of solid polymers containing the therapeutic agent.

Sustained-release capsules can, depending on their chemical nature, release the peptides or peptidomimetics for a few weeks up to over 100 days. Depending on the chemical nature and the biological stability of the therapeutic reagent, additional strategies for protein stabilization can be employed.

As the peptides or peptidomimetics of the invention can contain charged side chains or termini, they can be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

The agents of the invention are used in an amount effective to achieve the intended purpose. A therapeutically effective amount means an amount of agent sufficient to eliminate, reduce or inhibit worsening of at least one sign and/or symptoms of anxiety or a subtype thereof in patient presently experiencing symptoms of anxiety. For example, an amount is considered therapeutically effective if it significantly reduces at least one sign or symptom of anxiety in a population of treated patients (human or animal) compared with a control population of untreated patients. The amount is also considered therapeutically effective if an individual treated patient achieves an outcome more favorable than the mean outcome in a control population of comparable patients not treated by methods of the invention. A prophylactically effective amount of an agent means an amount of agent sufficient to delay, inhibit or prevent development of at least one sign or symptom of anxiety or a subtype thereof in a patient not currently experiencing symptoms but who is considered at heightened risk relative to the general population of developing such symptoms. For example, an amount is considered to be prophylactically effective if a population of patients at risk of developing symptoms of anxiety treated with the agent develops reduced signs or symptoms relative to a control population not treated with the agent. Reference to an effective amount means either a therapeutically or prophylactically effective amount. Reference to an effective regime means a combination of an effective amount and dosing frequency required to achieve the intended purpose as described above.

Preferred dosage ranges include 0.001 to 20 mol agent per kg patient body weight, optionally 0.03 to 3 µmol agent per kg patient body weight to µmol agent per kg patient body weight within 6 hours of stroke. In some methods, 0.1-20 µmol agent per kg patient body weight within 6 hours are administered. In some methods, 0.1-10 µmol agent per kg patient body weight is administered within 6 hours, more preferably about 0.3 µmol agent per kg patient body weight within 6 hours. In other instances, the dosages range is from 0.005 to 0.5 µmol agent per kg patient body weight. Dosage per kg body weight can be converted from rats to humans by dividing by 6.2 to compensate for different surface area to mass ratios. Dosages can be converted from units of moles to grams by multiplying by the molar weight of a peptide. Suitable dosages of peptides or peptidomimetics of the invention for use in humans can include 0.001 to 5 mg/kg patient body weight, or more preferably 0.005 to 1 mg/kg patient body weight or 0.05 to 1 mg/kg, or 0.09 to 0.9 mg/kg. In absolute weight for a 75 kg patient, these dosages translate to 0.075-375 mg, 0.375 to 75 mg or 3.75 mg to 75 mg or 6.7 to 67 mg. Rounded to encompass variations in e.g., patient weight, the dosage is usually within 0.05 to 500 mg, preferably 0.1 to 100 mg, 0.5 to 50 mg, or 1-20 mg.

The amount of agent administered depends on the subject being treated, on the subject's weight, the severity of the affliction, the manner of administration and the judgment of the prescribing physician. The therapy can be repeated intermittently while symptoms detectable or even when they are not detectable. The therapy can be provided alone or in combination with other drugs.

Therapeutically effective dose of the agents can provide therapeutic benefit without causing substantial toxicity. Toxicity of the peptides or peptidomimetics can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Peptides or peptidomimetics exhibiting high therapeutic indices are preferred (see, e.g., Fingl et al., 1975, In: *The Pharmacological Basis of Therapeutics*, Ch. 1, p. 1).

VIII. Screening Methods

The invention further provides methods of screening peptides, peptidomimetics and other compounds for activity useful in treating anxiety. Compounds are administered to an animal model of anxiety. Anxiety can be induced by placing an animal, such as a rat, in an unfamiliar environment and observing a response (e.g., crossing a grid of lines or selecting open or closed tubes), such as described in the Examples.

Compounds suitable for screening in the methods include peptides, peptidomimetics and small molecules (i.e., less than 500 Da) known to inhibit interactions of PSD-95 and NDMAR 2B. Other peptides, peptidomimetics and small molecules known to inhibit interactions between other pairs of NDMAR and PDZ domain proteins shown in Table 1 can also be screened.

Compounds to be screened can be both naturally occurring and synthetic, organic and inorganic, and including polymers (e.g., oligopeptides, polypeptides, oligonucleotides, and polynucleotides), small molecules, antibodies, sugars, fatty acids, nucleotides and nucleotide analogs, analogs of naturally occurring structures (e.g., peptide mimetics, nucleic acid analogs, and the like), and numerous other compounds. Compounds can be prepared from diversity libraries, such as random or combinatorial peptide or non-peptide libraries. Libraries include chemically synthesized libraries, recombinant (e.g., phage display libraries), and in vitro translation-based libraries. Examples of chemically synthesized libraries are described in Fodor et al., 1991, *Science* 251:767-773; Houghten et al., 1991, *Nature* 354:84-86; Lam et al., 1991, *Nature* 354:82-84; Medynski, 1994, *Bio/Technology* 12:709-710; Gallop et al., 1994, *J. Medicinal Chemistry* 37(9):1233-1251; Ohlmeyer et al., 1993, *Proc. Natl. Acad. Sci. USA* 90:10922-10926; Erb et al., 1994, *Proc. Natl. Acad. Sci. USA* 91:11422-11426; Houghten et al., 1992, *Biotechniques* 13:412; Jayawickreme et al., 1994, *Proc. Natl. Acad. Sci. USA* 91:1614-1618; Salmon et al., 1993, *Proc. Natl. Acad. Sci. USA* 90:11708-11712; WO 93/20242; and Brenner and Lerner, 1992, *Proc. Natl. Acad. Sci. USA* 89:5381-5383. Examples of phage display libraries are described in Scott and Smith, 1990, *Science* 249:386-390; Devlin et al., 1990, *Science,* 249:404-406; Christian, R. B., et al., 1992, *J. Mol. Biol.* 227:711-718); Lenstra, 1992, *J. Immunol. Meth.* 152: 149-157; Kay et al., 1993, *Gene* 128:59-65; WO 94/18318 dated Aug. 18, 1994. In vitro translation-based libraries include those described in WO 91/05058; and Mattheakis et al., 1994, *Proc. Natl. Acad. Sci. USA* 91:9022-9026. By way of examples of nonpeptide libraries, a benzodiazepine library (see e.g., Bunin et al., 1994, *Proc. Natl. Acad. Sci. USA* 91:4708-4712) can be adapted for use. Peptoid libraries (Simon et al., 1992, *Proc. Natl. Acad. Sci. USA* 89:9367-9371) can also be used. Another example of a library that can be used, in which the amide functionalities in peptides have been permethylated to generate a chemically transformed combinatorial library, is described by Ostresh et al. (1994, *Proc. Natl. Acad. Sci. USA* 91:11138-11142).

EXAMPLES

Methods

Experiments were performed in male adult Sprague-Dawley rats weighing 250-325 g (Charles River Laboratory, Canada). All procedures conformed to guidelines established by the Canadian Council on Animal Care and with the approval of the University of Prince Edward Island animal care committee. All animals were housed in groups of 2-3 animals in cages with free access to food and water and in rooms having an ambient temperature of $21 \pm 1°$ C. and 12:12 hr light/dark cycle.

90 min after undergoing an injection of NA-1 (or saline vehicle) via the tail vein under isoflurane/oxygen anesthesia, rats were tested in an open field arena to determine both state of arousal and ability to habituate to a novel environment. Also, rats were tested in the elevated plus maze. This maze was used to assess anxiety/emotionality in rats. The maze consisted of 4 arms (two open, two closed: 15 cm width and 60 cm length) extending from a central platform and elevated 1.5 m from the floor. Rats were placed in the centre of the maze and given free choice to enter any arm; operationally defined as having head and forepaws in an arm. Time spent in either the open or closed arms was recorded during a 10 min trial and scored (experimenter blind) from video recordings made simultaneously from two directions (overhead and horizontal).

Results

FIG. 1 shows mean habituation score ($\pm$SEM) during elevated plus maze testing. No significant differences were found for total time spent in the open arm during the 10 min trial (Saline 174.80$\pm$43.23; NA1 127.46$\pm$18.99). $t_{14}$=1.003, p=0.333). Habituation score was calculated as total time (seq) spent in the open arm during the last 5 minutes of the elevated plus maze minus the total time spent in the open arm during the first 5 min of the elevated plus maze. Saline (n=8); NA-1 (3 nmol/gram; n=8). $t_{14}$-2.49, p=0.026.

Figure 2:
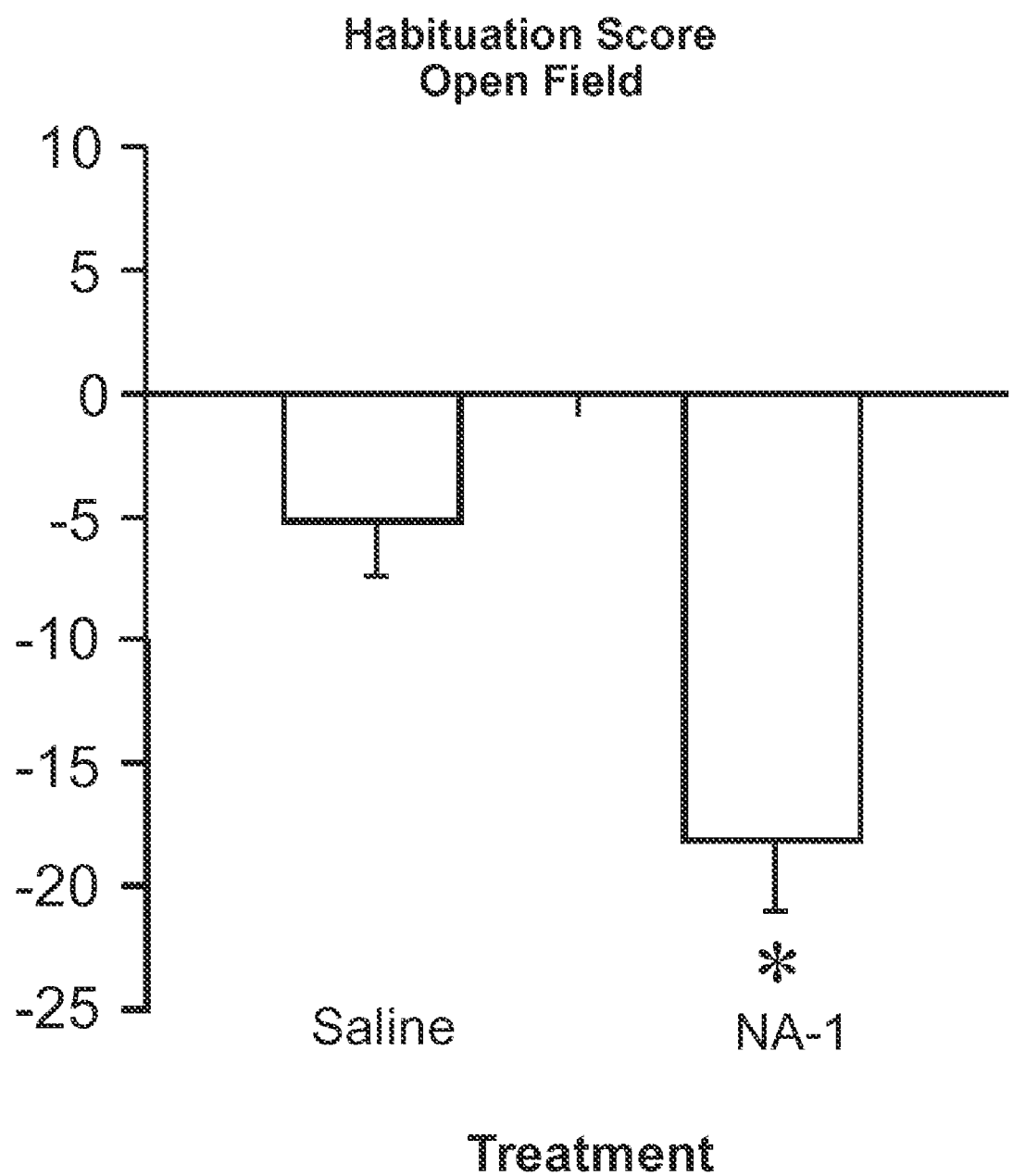
FIG. 2 shows mean habituation score (+SEM) during open field testing.

FIG. 2 shows mean habituation score ($\pm$SEM) during open field testing. No significant differences were found for total grid crosses during the 10 min trial (Saline: 37.13$\pm$6.4; NA-1: 28.88$\pm$6.62). $t_{14}$=0.896, p=0.385. Habituation score was calculated as total number of grids crossed during the last 5 min of the open field test minus the total number of grids crossed during the first 5 minutes of the open field test. Saline (n=8); NA-1 (3 nmol/gram; n=8). $T_{14}$=3.373, p=0.005.

It can be concluded from FIGS. 1 and 2 that treatment with NA-1 reduces the anxiety/emotionality levels of rats in two separate tests. Performance in the elevated plus maze was quantified as the mean amount of time spent in either a "closed" arm or an "open" arm; normally rats tend to avoid open spaces. Rats treated with NA-1 behaved similarly to rats treated with saline in the first 5 minutes of the assay. However, in the next 5 minutes, they exhibited greater amount of time in the open arm (reduced time in a closed arm) than rats treated with saline, suggesting that once they habituate to the test, they exhibit lower levels of anxiety (FIG. 1). Rats were also tested in an open field arena 90 min after the administration of NA-1 to determine both state of arousal and ability to habituate to a novel environment. They were scored for the total number of grid crosses during the 10 minute trial, as an index of exploratory behaviour which translates to arousal and habituation. As with the elevated plus maze, rats subjected to the Open Field testing also exhibited no differences between the controls (saline) and NA-1 treated groups in the first 5 min of the trial. Thereafter, however, rats treated with NA-1 exhibited improved habituation scores (reduced grid crosses) as compared with saline treated animals, suggesting that they habituated better to an open field environment.

Although the foregoing invention has been described in detail for purposes of clarity of understanding, it can be obvious that certain modifications can be practiced within the scope of the appended claims. All publications, documents, accession numbers and the like cited above are hereby incorporated by reference in their entirety for all purposes to the same extent as if each were so individually denoted. If more than one version of sequence is associated with the same accession number at different times, reference to that accession number means the version associated with it at the time of filing the present application dating back to any priority application that also includes that accession number. Unless otherwise apparent from the context, any step, feature, element or embodiment can be used in combination with any other.

What is claimed is:

1. A method of treating, or delaying or inhibiting development of at least one sign or symptom of anxiety in, a patient having or at risk of developing symptoms of anxiety, comprising administering to the patient an effective regime of an agent that inhibits specific binding of PSD95 to an NMDA receptor, wherein the agent is a chimeric peptide comprising an active peptide linked to an internalization peptide, wherein the active peptide is either:
   a) a peptide consisting of 3-25 amino acids from the C-terminus of an NMDA receptor or
   b) a PDZ domain 1 and/or 2 from a PSD-95 receptor,
wherein the patient is free of co-morbid stroke.

2. The method of claim 1, wherein the active peptide has an amino acid sequence comprising [E/D/N/Q]-[S/T]-[D/E/Q/N]-[V/L] (SEQ ID NO:1).

3. The method of claim 1, wherein the active peptide comprises an amino acid sequence selected from the group consisting of ESDV (SEQ ID NO:2), ESEV (SEQ ID NO:3), ETDV (SEQ ID NO:4), ETEV (SEQ ID NO:5), DTDV (SEQ ID NO:6), DTEV (SEQ ID NO:7).

4. The method of claim 1, wherein the active peptide has an amino acid sequence comprising KLSSIETDV (SEQ ID NO:8).

5. The method of claim 1, wherein the chimeric peptide has an amino acid comprising YGRKKRRQRRRKLSSIETDV (SEQ ID NO:9).

6. The method of claim 1, wherein the chimeric peptide has an amino acid sequence consisting of YGRKKRRQRRRKLSSIETDV (SEQ ID NO:9).

7. The method of claim 1, wherein the active peptide has an amino acid sequence comprising KLSSIESDV (SEQ ID NO:10).

8. The method of claim 1, wherein the chimeric peptide has an amino acid sequence comprising YGRKKRRQRRRKLSSIESDV (SEQ ID NO:11).

9. The method of claim 8, wherein the amino acid sequence consists of YGRKKRRQRRRKLSSIESDV (SEQ ID NO:11).

10. The method of claim 1, wherein the patient is free of diseases other than anxiety requiring treating with the agent.

11. The method of claim 1, wherein the patient is free of diseases other than anxiety mediated by excitotoxicity.

12. The method of claim 1, wherein the patient is free of diseases mediated by excitotoxicity.

13. The method of claim 1, wherein the agent is administered responsive to the patient having experienced an event promoting anxiety.

14. The method of claim 1, wherein the patient has an episode of acute anxiety.

15. The method of claim 1, wherein the patient is experiencing a panic disorder.

16. The method of claim 1, wherein the patient has a phobic disorder and is being exposed to or is about to be exposed to the phobia.

17. The method of claim 1, wherein the patient has social anxiety disorder and is being exposed to or is about to be exposed to a social situation that would trigger the disorder.

18. The method of claim 1, wherein the patient has an obsessive-compulsive disorder and is showing symptoms of the disorder.

19. The method of claim 1, wherein the patient has physical sensations of anxiety.

20. The method of claim 19, wherein the physical sensations comprise heart palpitations, nausea, chest pain, shortness of breath, and/or tension headache.

21. The method of claim 1, wherein the patient has post-traumatic stress syndrome.

22. The method of claim 1, wherein the patient has separation anxiety.

23. The method of claim 1, wherein the agent is administered responsive to the patient experiencing anxiety about a future event.

24. The method of claim 1, wherein the effective regime is administered responsive to diagnosis of anxiety in the patient.

25. The method of claim 1, further comprising administering a second regime effective for treatment or effecting prophylaxis of anxiety.

26. The method of claim 25, wherein the second regime comprises administering a second agent.

27. The method of claim 25, wherein the second regime comprises administering talk therapy.

28. The method of claim 1, wherein the patient is human.

29. The method of claim 1, wherein the agent is administered by intravenous infusion or subcutaneously.

30. The method of claim 1, wherein the effective regime is administered after diagnosis of a symptom of anxiety in the patient to relieve the symptom, or arrest or inhibit further development of the symptom.

31. The method of claim 1, wherein the agent is administered together with a pharmaceutically acceptable carrier as a pharmaceutical composition.

32. The method of claim 1, further comprising monitoring the patient to assess the effects of treatment on a symptom and/or sign of anxiety.

33. The method of claim 1, wherein the chimeric peptide is administered at a dose of 0.001 to 5 mg/kg body weight.

34. A method of treating, or delaying or inhibiting development of at least one sign or symptom of anxiety in, a patient suffering from or at risk of anxiety comprising administering to the patient an effective regime of a tSXV peptide linked to an internalization peptide, wherein the patient is free of co-morbid stroke.

* * * * *

SEQUENCE LISTING

<160> NUMBER OF SEQ ID NOS: 120

<210> SEQ ID NO 1
<211> LENGTH: 4
<212> TYPE: PRT
<213> ORGANISM: Artificial
<220> FEATURE:
<223> OTHER INFORMATION: Synthetic active peptide
<220> FEATURE:
<221> NAME/KEY: MOD_RES
<222> LOCATION: (1)..(1)
<223> OTHER INFORMATION: Xaa = Glu, Asp, Asn or Gln
<220> FEATURE:
<221> NAME/KEY: MOD_RES
<222> LOCATION: (2)..(2)
<223> OTHER INFORMATION: Xaa = Ser or Thr
<220> FEATURE:
<221> NAME/KEY: MOD_RES
<222> LOCATION: (3)..(3)
<223> OTHER INFORMATION: Xaa = Asp, Glu, Gln or Asn
<220> FEATURE:
<221> NAME/KEY: MOD_RES
<222> LOCATION: (4)..(4)
<223> OTHER INFORMATION: Xaa = Val or Leu

<400> SEQUENCE: 1

Xaa Xaa Xaa Xaa
1

<210> SEQ ID NO 2
<211> LENGTH: 4
<212> TYPE: PRT
<213> ORGANISM: Artificial
<220> FEATURE:
<223> OTHER INFORMATION: Synthetic active peptide

<400> SEQUENCE: 2

Glu Ser Asp Val
1

<210> SEQ ID NO 3
<211> LENGTH: 4
<212> TYPE: PRT
<213> ORGANISM: Artificial
<220> FEATURE:
<223> OTHER INFORMATION: Synthetic active peptide

<400> SEQUENCE: 3

Glu Ser Glu Val
1

<210> SEQ ID NO 4
<211> LENGTH: 4
<212> TYPE: PRT
<213> ORGANISM: Artificial
<220> FEATURE:
<223> OTHER INFORMATION: Synthetic active peptide

<400> SEQUENCE: 4

Glu Thr Asp Val
1

<210> SEQ ID NO 5
<211> LENGTH: 4
<212> TYPE: PRT
<213> ORGANISM: Artificial
<220> FEATURE:
<223> OTHER INFORMATION: Synthetic active peptide

```
<400> SEQUENCE: 5

Glu Thr Glu Val
1

<210> SEQ ID NO 6
<211> LENGTH: 4
<212> TYPE: PRT
<213> ORGANISM: Artificial
<220> FEATURE:
<223> OTHER INFORMATION: Synthetic active peptide

<400> SEQUENCE: 6

Asp Thr Asp Val
1

<210> SEQ ID NO 7
<211> LENGTH: 4
<212> TYPE: PRT
<213> ORGANISM: Artificial
<220> FEATURE:
<223> OTHER INFORMATION: Synthetic active peptide

<400> SEQUENCE: 7

Asp Thr Glu Val
1

<210> SEQ ID NO 8
<211> LENGTH: 9
<212> TYPE: PRT
<213> ORGANISM: Artificial
<220> FEATURE:
<223> OTHER INFORMATION: Synthetic active peptide

<400> SEQUENCE: 8

Lys Leu Ser Ser Ile Glu Thr Asp Val
1               5

<210> SEQ ID NO 9
<211> LENGTH: 20
<212> TYPE: PRT
<213> ORGANISM: Artificial
<220> FEATURE:
<223> OTHER INFORMATION: Synthetic chimeric peptide

<400> SEQUENCE: 9

Tyr Gly Arg Lys Lys Arg Arg Gln Arg Arg Lys Leu Ser Ser Ile
1               5                   10                  15

Glu Thr Asp Val
            20

<210> SEQ ID NO 10
<211> LENGTH: 9
<212> TYPE: PRT
<213> ORGANISM: Artificial
<220> FEATURE:
<223> OTHER INFORMATION: Synthetic active peptide

<400> SEQUENCE: 10

Lys Leu Ser Ser Ile Glu Ser Asp Val
1               5

<210> SEQ ID NO 11
<211> LENGTH: 20
<212> TYPE: PRT
<213> ORGANISM: Artificial
<220> FEATURE:
<223> OTHER INFORMATION: Synthetic chimeric peptide
```

```
<400> SEQUENCE: 11

Tyr Gly Arg Lys Lys Arg Arg Gln Arg Arg Lys Leu Ser Ser Ile
 1               5                  10                  15

Glu Ser Asp Val
            20

<210> SEQ ID NO 12
<211> LENGTH: 20
<212> TYPE: PRT
<213> ORGANISM: Artificial
<220> FEATURE:
<223> OTHER INFORMATION: Synthetic peptide

<400> SEQUENCE: 12

Phe Asn Gly Ser Ser Asn Gly His Val Tyr Glu Lys Leu Ser Ser Ile
 1               5                  10                  15

Glu Ser Asp Val
            20

<210> SEQ ID NO 13
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 13

His Pro Thr Asp Ile Thr Gly Pro Leu Asn Leu Ser Asp Pro Ser Val
 1               5                  10                  15

Ser Thr Val Val
            20

<210> SEQ ID NO 14
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 14

Arg Arg Ala Ile Glu Arg Glu Glu Gly Gln Leu Gln Leu Cys Ser Arg
 1               5                  10                  15

His Arg Glu Ser
            20

<210> SEQ ID NO 15
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 15

Thr Gln Gly Phe Pro Gly Pro Cys Thr Trp Arg Arg Ile Ser Ser Leu
 1               5                  10                  15

Glu Ser Glu Val
            20

<210> SEQ ID NO 16
<211> LENGTH: 20
<212> TYPE: PRT
<213> ORGANISM: Artificial
<220> FEATURE:
<223> OTHER INFORMATION: Synthetic peptide - C-terminal 20mer sequence
```

-continued

```
<400> SEQUENCE: 16

Ala Val Ser Arg Lys Thr Glu Leu Glu Glu Tyr Gln Arg Thr Ser Arg
1               5                   10                  15

Thr Cys Glu Ser
            20

<210> SEQ ID NO 17
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 17

Leu Asn Ser Cys Ser Asn Arg Arg Val Tyr Lys Lys Met Pro Ser Ile
1               5                   10                  15

Glu Ser Asp Val
            20

<210> SEQ ID NO 18
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 18

Gly Gly Asp Leu Gly Thr Arg Arg Gly Ser Ala His Phe Ser Ser Leu
1               5                   10                  15

Glu Ser Glu Val
            20

<210> SEQ ID NO 19
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 19

Gln Pro Thr Pro Thr Leu Gly Leu Asn Leu Gly Asn Asp Pro Asp Arg
1               5                   10                  15

Gly Thr Ser Ile
            20

<210> SEQ ID NO 20
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 20

Met Gln Ser Ile Pro Cys Met Ser His Ser Ser Gly Met Pro Leu Gly
1               5                   10                  15

Ala Thr Gly Leu
            20

<210> SEQ ID NO 21
<211> LENGTH: 20
<212> TYPE: PRT
<213> ORGANISM: Artificial
<220> FEATURE:
<223> OTHER INFORMATION: Synthetic peptide - C-terminal 20mer sequence
```

```
<400> SEQUENCE: 21

Gln Asn Phe Ala Thr Tyr Lys Glu Gly Tyr Asn Val Tyr Gly Ile Glu
1               5                   10                  15

Ser Val Lys Ile
            20

<210> SEQ ID NO 22
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 22

Gln Asn Tyr Ala Thr Tyr Arg Glu Gly Tyr Asn Val Tyr Gly Thr Glu
1               5                   10                  15

Ser Val Lys Ile
            20

<210> SEQ ID NO 23
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 23

His Thr Gly Thr Ala Ile Arg Gln Ser Ser Gly Leu Ala Val Ile Ala
1               5                   10                  15

Ser Asp Leu Pro
            20

<210> SEQ ID NO 24
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 24

Ser Phe Thr Ser Ile Leu Thr Cys His Gln Arg Arg Thr Gln Arg Lys
1               5                   10                  15

Glu Thr Val Ala
            20

<210> SEQ ID NO 25
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 25

Glu Val Ile Asn Met His Thr Phe Asn Asp Arg Arg Leu Pro Gly Lys
1               5                   10                  15

Glu Thr Met Ala
            20

<210> SEQ ID NO 26
<211> LENGTH: 20
<212> TYPE: PRT
<213> ORGANISM: Artificial
<220> FEATURE:
<223> OTHER INFORMATION: Synthetic peptide - C-terminal 20mer sequence
```

```
<400> SEQUENCE: 26

Arg Arg Leu Pro Gly Lys Asp Ser Met Ala Cys Ser Thr Ser Leu Ala
1               5                   10                  15

Pro Val Phe Pro
            20

<210> SEQ ID NO 27
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 27

Ser Thr Val Val
1

<210> SEQ ID NO 28
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 28

His Arg Glu Ser
1

<210> SEQ ID NO 29
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 29

Thr Cys Glu Ser
1

<210> SEQ ID NO 30
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 30

Gly Thr Ser Ile
1

<210> SEQ ID NO 31
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 31

Ala Thr Gly Leu
1

<210> SEQ ID NO 32
<211> LENGTH: 4
<212> TYPE: PRT
<213> ORGANISM: Artificial
<220> FEATURE:
```

-continued

```
<223> OTHER INFORMATION: Synthetic peptide - C-terminal 4mer sequence

<400> SEQUENCE: 32

Ser Val Lys Ile
1

<210> SEQ ID NO 33
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 33

Ser Asp Leu Pro
1

<210> SEQ ID NO 34
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 34

Glu Thr Val Ala
1

<210> SEQ ID NO 35
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 35

Glu Thr Met Ala
1

<210> SEQ ID NO 36
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 36

Pro Val Phe Pro
1

<210> SEQ ID NO 37
<211> LENGTH: 11
<212> TYPE: PRT
<213> ORGANISM: Artificial
<220> FEATURE:
<223> OTHER INFORMATION: Synthetic TAT internalization peptide

<400> SEQUENCE: 37

Tyr Gly Arg Lys Lys Arg Arg Gln Arg Arg
1               5                   10

<210> SEQ ID NO 38
<211> LENGTH: 11
<212> TYPE: PRT
<213> ORGANISM: Artificial
<220> FEATURE:
<223> OTHER INFORMATION: Synthetic  internalization peptide
<220> FEATURE:
```

```
<221> NAME/KEY: misc_feature
<222> LOCATION: (1)..(1)
<223> OTHER INFORMATION: Xaa can be any naturally occurring amino acid

<400> SEQUENCE: 38

Xaa Gly Arg Lys Lys Arg Arg Gln Arg Arg
1               5                   10

<210> SEQ ID NO 39
<211> LENGTH: 11
<212> TYPE: PRT
<213> ORGANISM: Artificial
<220> FEATURE:
<223> OTHER INFORMATION: Synthetic tat variant internalization peptide

<400> SEQUENCE: 39

Phe Gly Arg Lys Lys Arg Arg Gln Arg Arg
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic tat variant internalization peptide

<400> SEQUENCE: 40

Gly Arg Lys Lys Arg Arg Gln Arg Arg
1               5                   10

<210> SEQ ID NO 41
<211> LENGTH: 5
<212> TYPE: PRT
<213> ORGANISM: Artificial
<220> FEATURE:
<223> OTHER INFORMATION: Synthetic peptide

<400> SEQUENCE: 41

Gly Ser Ser Ser Ser
1               5

<210> SEQ ID NO 42
<211> LENGTH: 5
<212> TYPE: PRT
<213> ORGANISM: Artificial
<220> FEATURE:
<223> OTHER INFORMATION: Synthetic peptide

<400> SEQUENCE: 42

Thr Gly Glu Lys Pro
1               5

<210> SEQ ID NO 43
<211> LENGTH: 8
<212> TYPE: PRT
<213> ORGANISM: Artificial
<220> FEATURE:
<223> OTHER INFORMATION: Synthetic peptide

<400> SEQUENCE: 43

Gly Gly Arg Arg Gly Gly Gly Ser
1               5

<210> SEQ ID NO 44
<211> LENGTH: 9
<212> TYPE: PRT
<213> ORGANISM: Artificial
<220> FEATURE:
```

```
<223> OTHER INFORMATION: Synthetic peptide

<400> SEQUENCE: 44

Leu Arg Gln Arg Asp Gly Glu Arg Pro
1               5

<210> SEQ ID NO 45
<211> LENGTH: 20
<212> TYPE: PRT
<213> ORGANISM: Artificial
<220> FEATURE:
<223> OTHER INFORMATION: Synthetic peptide

<400> SEQUENCE: 45

Phe Gly Arg Lys Lys Arg Arg Gln Arg Arg Lys Leu Ser Ser Ile
1               5                   10                  15

Glu Ser Asp Val
            20

<210> SEQ ID NO 46
<211> LENGTH: 19
<212> TYPE: PRT
<213> ORGANISM: Artificial
<220> FEATURE:
<223> OTHER INFORMATION: Synthetic peptide

<400> SEQUENCE: 46

Gly Lys Lys Lys Lys Lys Gln Lys Lys Lys Leu Ser Ser Ile Glu
1               5                   10                  15

Ser Asp Val

<210> SEQ ID NO 47
<211> LENGTH: 18
<212> TYPE: PRT
<213> ORGANISM: Artificial
<220> FEATURE:
<223> OTHER INFORMATION: Synthetic peptide

<400> SEQUENCE: 47

Arg Lys Lys Arg Arg Gln Arg Arg Lys Leu Ser Ser Ile Glu Ser
1               5                   10                  15

Asp Val

<210> SEQ ID NO 48
<211> LENGTH: 19
<212> TYPE: PRT
<213> ORGANISM: Artificial
<220> FEATURE:
<223> OTHER INFORMATION: Synthetic peptide

<400> SEQUENCE: 48

Gly Ala Lys Lys Arg Arg Gln Arg Arg Arg Lys Leu Ser Ser Ile Glu
1               5                   10                  15

Ser Asp Val

<210> SEQ ID NO 49
<211> LENGTH: 18
<212> TYPE: PRT
<213> ORGANISM: Artificial
<220> FEATURE:
<223> OTHER INFORMATION: Synthetic peptide

<400> SEQUENCE: 49

Ala Lys Lys Arg Arg Gln Arg Arg Arg Lys Leu Ser Ser Ile Glu Ser
1               5                   10                  15
```

Asp Val

<210> SEQ ID NO 50
<211> LENGTH: 19
<212> TYPE: PRT
<213> ORGANISM: Artificial
<220> FEATURE:
<223> OTHER INFORMATION: Synthetic peptide

<400> SEQUENCE: 50

Gly Arg Lys Ala Arg Arg Gln Arg Arg Arg Lys Leu Ser Ser Ile Glu
1               5                   10                  15

Ser Asp Val

<210> SEQ ID NO 51
<211> LENGTH: 18
<212> TYPE: PRT
<213> ORGANISM: Artificial
<220> FEATURE:
<223> OTHER INFORMATION: Synthetic peptide

<400> SEQUENCE: 51

Arg Lys Ala Arg Arg Gln Arg Arg Arg Lys Leu Ser Ser Ile Glu Ser
1               5                   10                  15

Asp Val

<210> SEQ ID NO 52
<211> LENGTH: 19
<212> TYPE: PRT
<213> ORGANISM: Artificial
<220> FEATURE:
<223> OTHER INFORMATION: Synthetic peptide

<400> SEQUENCE: 52

Gly Arg Lys Lys Ala Arg Gln Arg Arg Arg Lys Leu Ser Ser Ile Glu
1               5                   10                  15

Ser Asp Val

<210> SEQ ID NO 53
<211> LENGTH: 18
<212> TYPE: PRT
<213> ORGANISM: Artificial
<220> FEATURE:
<223> OTHER INFORMATION: Synthetic peptide

<400> SEQUENCE: 53

Arg Lys Lys Ala Arg Gln Arg Arg Arg Lys Leu Ser Ser Ile Glu Ser
1               5                   10                  15

Asp Val

<210> SEQ ID NO 54
<211> LENGTH: 19
<212> TYPE: PRT
<213> ORGANISM: Artificial
<220> FEATURE:
<223> OTHER INFORMATION: Synthetic peptide

<400> SEQUENCE: 54

Gly Arg Lys Lys Arg Arg Gln Ala Arg Arg Lys Leu Ser Ser Ile Glu
1               5                   10                  15

Ser Asp Val

<210> SEQ ID NO 55

```
<211> LENGTH: 18
<212> TYPE: PRT
<213> ORGANISM: Artificial
<220> FEATURE:
<223> OTHER INFORMATION: Synthetic peptide

<400> SEQUENCE: 55

Arg Lys Lys Arg Arg Gln Ala Arg Arg Lys Leu Ser Ser Ile Glu Ser
1               5                   10                  15

Asp Val

<210> SEQ ID NO 56
<211> LENGTH: 19
<212> TYPE: PRT
<213> ORGANISM: Artificial
<220> FEATURE:
<223> OTHER INFORMATION: Synthetic peptide

<400> SEQUENCE: 56

Gly Arg Lys Lys Arg Arg Gln Arg Ala Arg Lys Leu Ser Ser Ile Glu
1               5                   10                  15

Ser Asp Val

<210> SEQ ID NO 57
<211> LENGTH: 18
<212> TYPE: PRT
<213> ORGANISM: Artificial
<220> FEATURE:
<223> OTHER INFORMATION: Synthetic peptide

<400> SEQUENCE: 57

Arg Lys Lys Arg Arg Gln Arg Ala Arg Lys Leu Ser Ser Ile Glu Ser
1               5                   10                  15

Asp Val

<210> SEQ ID NO 58
<211> LENGTH: 20
<212> TYPE: PRT
<213> ORGANISM: Artificial
<220> FEATURE:
<223> OTHER INFORMATION: Synthetic peptide

<400> SEQUENCE: 58

Arg Arg Pro Arg Arg Pro Arg Arg Pro Arg Arg Lys Leu Ser Ser Ile
1               5                   10                  15

Glu Ser Asp Val
            20

<210> SEQ ID NO 59
<211> LENGTH: 20
<212> TYPE: PRT
<213> ORGANISM: Artificial
<220> FEATURE:
<223> OTHER INFORMATION: Synthetic peptide

<400> SEQUENCE: 59

Arg Arg Ala Arg Arg Ala Arg Arg Ala Arg Arg Lys Leu Ser Ser Ile
1               5                   10                  15

Glu Ser Asp Val
            20

<210> SEQ ID NO 60
<211> LENGTH: 19
<212> TYPE: PRT
<213> ORGANISM: Artificial
```

```
<220> FEATURE:
<223> OTHER INFORMATION: Synthetic peptide

<400> SEQUENCE: 60

Arg Arg Arg Ala Arg Arg Ala Arg Arg Lys Leu Ser Ser Ile Glu
1               5                   10                  15

Ser Asp Val

<210> SEQ ID NO 61
<211> LENGTH: 19
<212> TYPE: PRT
<213> ORGANISM: Artificial
<220> FEATURE:
<223> OTHER INFORMATION: Synthetic peptide

<400> SEQUENCE: 61

Arg Arg Arg Pro Arg Arg Arg Pro Arg Arg Lys Leu Ser Ser Ile Glu
1               5                   10                  15

Ser Asp Val

<210> SEQ ID NO 62
<211> LENGTH: 17
<212> TYPE: PRT
<213> ORGANISM: Artificial
<220> FEATURE:
<223> OTHER INFORMATION: Synthetic peptide

<400> SEQUENCE: 62

Arg Arg Pro Arg Arg Pro Arg Arg Lys Leu Ser Ser Ile Glu Ser Asp
1               5                   10                  15

Val

<210> SEQ ID NO 63
<211> LENGTH: 17
<212> TYPE: PRT
<213> ORGANISM: Artificial
<220> FEATURE:
<223> OTHER INFORMATION: Synthetic peptide

<400> SEQUENCE: 63

Arg Arg Ala Arg Arg Ala Arg Arg Lys Leu Ser Ser Ile Glu Ser Asp
1               5                   10                  15

Val

<210> SEQ ID NO 64
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Phe modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 64

Xaa Gly Arg Lys Lys Arg Arg Gln Arg Arg Lys Leu Ser Ser Ile
1               5                   10                  15

Glu Ser Asp Val
            20

<210> SEQ ID NO 65
```

```
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 65

Xaa Phe Gly Arg Lys Lys Arg Arg Gln Arg Arg Lys Leu Ser Ser
1               5                   10                  15

Ile Glu Ser Asp Val
            20

<210> SEQ ID NO 66
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 66

Xaa Phe Gly Arg Lys Lys Arg Arg Gln Arg Arg Lys Leu Ser Ser
1               5                   10                  15

Ile Glu Ser Asp Val
            20

<210> SEQ ID NO 67
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 67

Xaa Lys Lys Lys Lys Lys Gln Lys Lys Lys Leu Ser Ser Ile Glu
1               5                   10                  15

Ser Asp Val

<210> SEQ ID NO 68
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 68

Xaa Gly Lys Lys Lys Lys Lys Gln Lys Lys Lys Leu Ser Ser Ile
1               5                   10                  15

Glu Ser Asp Val
            20
```

```
<210> SEQ ID NO 69
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 69

Xaa Gly Lys Lys Lys Lys Gln Lys Lys Lys Lys Leu Ser Ser Ile
1               5                   10                  15

Glu Ser Asp Val
            20

<210> SEQ ID NO 70
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule
      or other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 70

Xaa Lys Lys Arg Arg Gln Arg Arg Arg Lys Leu Ser Ser Ile Glu Ser
1               5                   10                  15

Asp Val

<210> SEQ ID NO 71
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 71

Xaa Arg Lys Lys Arg Arg Gln Arg Arg Arg Lys Leu Ser Ser Ile Glu
1               5                   10                  15

Ser Asp Val

<210> SEQ ID NO 72
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 72

Xaa Arg Lys Lys Arg Arg Gln Arg Arg Arg Lys Leu Ser Ser Ile Glu
1               5                   10                  15

Ser Asp Val
```

<210> SEQ ID NO 73
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 73

Xaa Ala Lys Lys Arg Arg Gln Arg Arg Lys Leu Ser Ser Ile Glu
1               5                   10                  15

Ser Asp Val

<210> SEQ ID NO 74
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 74

Xaa Gly Ala Lys Lys Arg Arg Gln Arg Arg Lys Leu Ser Ser Ile
1               5                   10                  15

Glu Ser Asp Val
            20

<210> SEQ ID NO 75
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 75

Xaa Gly Ala Lys Lys Arg Arg Gln Arg Arg Lys Leu Ser Ser Ile
1               5                   10                  15

Glu Ser Asp Val
            20

<210> SEQ ID NO 76
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Ala modified by a biotin molecule
      or other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 76

Xaa Lys Lys Arg Arg Gln Arg Arg Lys Leu Ser Ser Ile Glu Ser

```
                  1               5                  10                  15

Asp Val

<210> SEQ ID NO 77
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 77

Xaa Ala Lys Lys Arg Arg Gln Arg Arg Arg Lys Leu Ser Ser Ile Glu
  1               5                  10                  15

Ser Asp Val

<210> SEQ ID NO 78
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 78

Xaa Ala Lys Lys Arg Arg Gln Arg Arg Arg Lys Leu Ser Ser Ile Glu
  1               5                  10                  15

Ser Asp Val

<210> SEQ ID NO 79
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 79

Xaa Arg Lys Ala Arg Arg Gln Arg Arg Arg Lys Leu Ser Ser Ile Glu
  1               5                  10                  15

Ser Asp Val

<210> SEQ ID NO 80
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 80

Xaa Gly Arg Lys Ala Arg Arg Gln Arg Arg Arg Lys Leu Ser Ser Ile
  1               5                  10                  15
```

```
Glu Ser Asp Val
        20

<210> SEQ ID NO 81
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 81

Xaa Gly Arg Lys Ala Arg Arg Gln Arg Arg Lys Leu Ser Ser Ile
1               5                   10                  15

Glu Ser Asp Val
        20

<210> SEQ ID NO 82
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 82

Xaa Lys Ala Arg Arg Gln Arg Arg Arg Lys Leu Ser Ser Ile Glu Ser
1               5                   10                  15

Asp Val

<210> SEQ ID NO 83
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 83

Xaa Arg Lys Ala Arg Arg Gln Arg Arg Arg Lys Leu Ser Ser Ile Glu
1               5                   10                  15

Ser Asp Val

<210> SEQ ID NO 84
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 84

Xaa Arg Lys Ala Arg Arg Gln Arg Arg Arg Lys Leu Ser Ser Ile Glu
```

```
1               5                   10                  15
Ser Asp Val

<210> SEQ ID NO 85
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 85

Xaa Arg Lys Lys Ala Arg Gln Arg Arg Arg Lys Leu Ser Ser Ile Glu
1               5                   10                  15

Ser Asp Val

<210> SEQ ID NO 86
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 86

Xaa Gly Arg Lys Lys Ala Arg Gln Arg Arg Arg Lys Leu Ser Ser Ile
1               5                   10                  15

Glu Ser Asp Val
            20

<210> SEQ ID NO 87
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 87

Xaa Gly Arg Lys Lys Ala Arg Gln Arg Arg Arg Lys Leu Ser Ser Ile
1               5                   10                  15

Glu Ser Asp Val
            20

<210> SEQ ID NO 88
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.
```

```
<400> SEQUENCE: 88

Xaa Lys Lys Ala Arg Gln Arg Arg Arg Lys Leu Ser Ser Ile Glu Ser
1               5                   10                  15

Asp Val

<210> SEQ ID NO 89
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 89

Xaa Arg Lys Lys Ala Arg Gln Arg Arg Arg Lys Leu Ser Ser Ile Glu
1               5                   10                  15

Ser Asp Val

<210> SEQ ID NO 90
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 90

Xaa Arg Lys Lys Ala Arg Gln Arg Arg Arg Lys Leu Ser Ser Ile Glu
1               5                   10                  15

Ser Asp Val

<210> SEQ ID NO 91
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 91

Xaa Arg Lys Lys Arg Arg Gln Ala Arg Arg Lys Leu Ser Ser Ile Glu
1               5                   10                  15

Ser Asp Val

<210> SEQ ID NO 92
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate
```

```
<400> SEQUENCE: 92

Xaa Gly Arg Lys Lys Arg Arg Gln Ala Arg Arg Lys Leu Ser Ser Ile
1               5                   10                  15

Glu Ser Asp Val
            20

<210> SEQ ID NO 93
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 93

Xaa Gly Arg Lys Lys Arg Arg Gln Ala Arg Arg Lys Leu Ser Ser Ile
1               5                   10                  15

Glu Ser Asp Val
            20

<210> SEQ ID NO 94
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 94

Xaa Lys Lys Arg Arg Gln Ala Arg Arg Lys Leu Ser Ser Ile Glu Ser
1               5                   10                  15

Asp Val

<210> SEQ ID NO 95
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 95

Xaa Arg Lys Lys Arg Arg Gln Ala Arg Arg Lys Leu Ser Ser Ile Glu
1               5                   10                  15

Ser Asp Val

<210> SEQ ID NO 96
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr
```

```
<400> SEQUENCE: 96

Xaa Arg Lys Lys Arg Arg Gln Ala Arg Arg Lys Leu Ser Ser Ile Glu
1               5                   10                  15

Ser Asp Val

<210> SEQ ID NO 97
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 97

Xaa Arg Lys Lys Arg Arg Gln Arg Ala Arg Lys Leu Ser Ser Ile Glu
1               5                   10                  15

Ser Asp Val

<210> SEQ ID NO 98
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 98

Xaa Gly Arg Lys Lys Arg Arg Gln Arg Ala Arg Lys Leu Ser Ser Ile
1               5                   10                  15

Glu Ser Asp Val
            20

<210> SEQ ID NO 99
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 99

Xaa Gly Arg Lys Lys Arg Arg Gln Arg Ala Arg Lys Leu Ser Ser Ile
1               5                   10                  15

Glu Ser Asp Val
            20

<210> SEQ ID NO 100
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 100

Xaa Lys Lys Arg Arg Gln Arg Ala Arg Lys Leu Ser Ser Ile Glu Ser
1               5                   10                  15

Asp Val

<210> SEQ ID NO 101
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 101

Xaa Arg Lys Lys Arg Arg Gln Arg Ala Arg Lys Leu Ser Ser Ile Glu
1               5                   10                  15

Ser Asp Val

<210> SEQ ID NO 102
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 102

Xaa Arg Lys Lys Arg Arg Gln Arg Ala Arg Lys Leu Ser Ser Ile Glu
1               5                   10                  15

Ser Asp Val

<210> SEQ ID NO 103
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 103

Xaa Arg Pro Arg Arg Pro Arg Arg Pro Arg Arg Lys Leu Ser Ser Ile
1               5                   10                  15

Glu Ser Asp Val
            20

<210> SEQ ID NO 104
<211> LENGTH: 21
<212> TYPE: PRT
<213> ORGANISM: Artificial
<220> FEATURE:
<223> OTHER INFORMATION: Synthetic peptide
```

```
<220> FEATURE:
<221> NAME/KEY: MISC_FEATURE
<222> LOCATION: (1)..(1)
<223> OTHER INFORMATION: Xaa is pyroglutamate

<400> SEQUENCE: 104

Xaa Arg Arg Pro Arg Arg Pro Arg Arg Pro Arg Arg Lys Leu Ser Ser
1               5                   10                  15

Ile Glu Ser Asp Val
            20

<210> SEQ ID NO 105
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 105

Xaa Arg Arg Pro Arg Arg Pro Arg Arg Pro Arg Arg Lys Leu Ser Ser
1               5                   10                  15

Ile Glu Ser Asp Val
            20

<210> SEQ ID NO 106
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 106

Xaa Arg Ala Arg Arg Ala Arg Arg Ala Arg Arg Lys Leu Ser Ser Ile
1               5                   10                  15

Glu Ser Asp Val
            20

<210> SEQ ID NO 107
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 107

Xaa Arg Arg Ala Arg Arg Ala Arg Arg Ala Arg Arg Lys Leu Ser Ser
1               5                   10                  15

Ile Glu Ser Asp Val
            20

<210> SEQ ID NO 108
<211> LENGTH: 21
<212> TYPE: PRT
```

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 108

Xaa Arg Arg Ala Arg Arg Ala Arg Arg Ala Arg Arg Lys Leu Ser Ser
1               5                   10                  15

Ile Glu Ser Asp Val
            20

<210> SEQ ID NO 109
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 109

Xaa Arg Arg Ala Arg Arg Arg Ala Arg Arg Lys Leu Ser Ser Ile Glu
1               5                   10                  15

Ser Asp Val

<210> SEQ ID NO 110
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 110

Xaa Arg Arg Arg Ala Arg Arg Ala Arg Arg Lys Leu Ser Ser Ile
1               5                   10                  15

Glu Ser Asp Val
            20

<210> SEQ ID NO 111
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 111

Xaa Arg Arg Arg Ala Arg Arg Arg Ala Arg Arg Lys Leu Ser Ser Ile
1               5                   10                  15

Glu Ser Asp Val
            20

<210> SEQ ID NO 112
```

```
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 112

Xaa Arg Arg Pro Arg Arg Arg Pro Arg Arg Lys Leu Ser Ser Ile Glu
1               5                   10                  15

Ser Asp Val

<210> SEQ ID NO 113
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 113

Xaa Arg Arg Arg Pro Arg Arg Arg Pro Arg Arg Lys Leu Ser Ser Ile
1               5                   10                  15

Glu Ser Asp Val
            20

<210> SEQ ID NO 114
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 114

Xaa Arg Arg Arg Pro Arg Arg Arg Pro Arg Arg Lys Leu Ser Ser Ile
1               5                   10                  15

Glu Ser Asp Val
            20

<210> SEQ ID NO 115
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 115

Xaa Arg Pro Arg Arg Pro Arg Arg Lys Leu Ser Ser Ile Glu Ser Asp
1               5                   10                  15
```

Val

<210> SEQ ID NO 116
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 116

Xaa Arg Arg Pro Arg Arg Pro Arg Arg Lys Leu Ser Ser Ile Glu Ser
1               5                   10                  15

Asp Val

<210> SEQ ID NO 117
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 117

Xaa Arg Arg Pro Arg Arg Pro Arg Arg Lys Leu Ser Ser Ile Glu Ser
1               5                   10                  15

Asp Val

<210> SEQ ID NO 118
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 118

Xaa Arg Ala Arg Arg Ala Arg Arg Lys Leu Ser Ser Ile Glu Ser Asp
1               5                   10                  15

Val

<210> SEQ ID NO 119
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 119

Xaa Arg Arg Ala Arg Arg Ala Arg Arg Lys Leu Ser Ser Ile Glu Ser
1               5                   10                  15

Asp Val

```
<210> SEQ ID NO 120
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 120

Xaa Arg Arg Ala Arg Arg Ala Arg Arg Lys Leu Ser Ser Ile Glu Ser
1               5                   10                  15

Asp Val
```